US009216226B2

(12) United States Patent
Ladet et al.

(10) Patent No.: US 9,216,226 B2
(45) Date of Patent: Dec. 22, 2015

(54) COMPOUNDS AND MEDICAL DEVICES ACTIVATED WITH SOLVOPHOBIC LINKERS

(71) Applicant: Sofradim Production, Trévoux (FR)

(72) Inventors: Sébastien Ladet, Caluire & Cuire (FR); Philippe Gravagna, Charnoz (FR)

(73) Assignee: Sofradim Production (FR)

( * ) Notice: Subject to any disclaimer, the term of this patent is extended or adjusted under 35 U.S.C. 154(b) by 0 days.

(21) Appl. No.: 14/612,353

(22) Filed: Feb. 3, 2015

(65) Prior Publication Data

US 2015/0147395 A1    May 28, 2015

Related U.S. Application Data

(62) Division of application No. 13/202,366, filed as application No. PCT/IB2010/000630 on Feb. 22, 2010, now Pat. No. 8,969,473.

(60) Provisional application No. 61/154,374, filed on Feb. 21, 2009.

(51) Int. Cl.

| A61K 47/48 | (2006.01) |
| A61K 47/30 | (2006.01) |
| A61L 27/26 | (2006.01) |
| A61L 27/48 | (2006.01) |
| A61L 27/50 | (2006.01) |
| A61L 27/54 | (2006.01) |
| A61L 31/14 | (2006.01) |
| A61L 31/16 | (2006.01) |

(52) U.S. Cl.
CPC ............ *A61K 47/48092* (2013.01); *A61K 47/30* (2013.01); *A61L 27/26* (2013.01); *A61L 27/48* (2013.01); *A61L 27/50* (2013.01); *A61L 27/54* (2013.01); *A61L 31/14* (2013.01); *A61L 31/16* (2013.01); *A61L 2300/00* (2013.01)

(58) Field of Classification Search
CPC .................... A61K 47/48092; A61K 47/30
See application file for complete search history.

(56) References Cited

U.S. PATENT DOCUMENTS

| 3,767,085 A | 10/1973 | Cannon et al. |
| 4,326,532 A | 4/1982 | Hammar |
| 4,359,049 A | 11/1982 | Redl et al. |
| 4,464,321 A | 8/1984 | Pittalis et al. |
| 4,538,920 A | 9/1985 | Drake |
| 4,753,536 A | 6/1988 | Spehar et al. |
| 4,839,345 A | 6/1989 | Doi et al. |
| 4,857,403 A | 8/1989 | De Lucca et al. |
| 4,880,662 A | 11/1989 | Habrich et al. |
| 5,021,207 A | 6/1991 | De Lucca et al. |
| 5,372,585 A | 12/1994 | Tiefenbrun et al. |
| 5,455,308 A | 10/1995 | Bastiaansen |
| 5,562,946 A | 10/1996 | Fofonoff et al. |
| 5,578,662 A | 11/1996 | Bennett et al. |
| 5,582,955 A | 12/1996 | Keana et al. |
| 5,612,050 A | 3/1997 | Rowe et al. |
| 5,804,318 A | 9/1998 | Pinchuk et al. |
| 5,911,942 A | 6/1999 | Fofonoff et al. |
| 6,099,563 A | 8/2000 | Zhong |
| 6,107,365 A | 8/2000 | Bertozzi et al. |
| 6,107,453 A | 8/2000 | Zuccato et al. |
| 6,312,725 B1 | 11/2001 | Wallace et al. |
| 6,342,591 B1 | 1/2002 | Zamora et al. |
| 6,451,032 B1 | 9/2002 | Ory et al. |
| 6,534,611 B1 | 3/2003 | Darling et al. |
| 6,552,103 B1 | 4/2003 | Bertozzi et al. |
| 6,570,040 B2 | 5/2003 | Saxon et al. |
| 6,576,000 B2 | 6/2003 | Carrison |
| 6,624,245 B2 | 9/2003 | Wallace et al. |
| 6,881,766 B2 | 4/2005 | Hain |
| 6,958,212 B1 | 10/2005 | Hubbell et al. |
| 7,012,126 B2 | 3/2006 | Matsuda et al. |
| 7,105,629 B2 | 9/2006 | Matsuda et al. |
| 7,122,703 B2 | 10/2006 | Saxon et al. |
| 7,144,976 B2 | 12/2006 | Matsuda et al. |
| 7,172,877 B2 | 2/2007 | Ting |
| 7,247,692 B2 | 7/2007 | Laredo |
| 7,294,357 B2 | 11/2007 | Roby |
| 7,371,719 B2 | 5/2008 | Stupp et al. |
| 7,375,234 B2 | 5/2008 | Sharpless et al. |
| 7,560,588 B2 | 7/2009 | Breitenkamp et al. |
| 7,618,944 B2 | 11/2009 | Breitenkamp et al. |
| 7,638,558 B2 | 12/2009 | Breitenkamp et al. |
| 7,667,012 B2 | 2/2010 | Saxon et al. |
| 7,795,355 B2 | 9/2010 | Matyjaszewski et al. |

(Continued)

FOREIGN PATENT DOCUMENTS

| BE | 1008260 A6 | 2/1996 |
| EP | 0490854 A2 | 6/1992 |

(Continued)

OTHER PUBLICATIONS

Jaeyoung Lee, Eun Chul Cho, Kilwon Cho J. Control. Release 94 (2004) 323-335.
Riva et al., Contribution of "Click Chemistry" to the synthesis of antimicrobial aliphatic copolyester. 2008, 49, pp. 2023-2028.
Shi et al., The immobilization of Proteins on Biodegradable Polymer Fibers via click Chemistry, Biomaterials 29 (2008), 1118-1126.
Yang et al. (J. Appl. Pol. Sci. 2004, 92, 1625-1632).
Aiba (Int. J. Macromol. 1991, 13, 40-44).
Shin et al. (J. Appl. Pol. Sci. 1999, 74, 2911-2916).
Q. Shi, et al., "The Immobilization of Proteins on Biodegradable Polymer Fibers via Click Chemistry", Biomaterials, 29, (2008), pp. 1118-1126.
Jerome, et al., "Recent Advances in the Synthesis of Aliphatic Polyesters Ring-Opening Polymerization", Advanced Drug Delivery Reviews, 60, (2008), pp. 1056-1076.

(Continued)

*Primary Examiner* — Johann R Richter
*Assistant Examiner* — Genevieve S Alley

(57) ABSTRACT

The present disclosure relates to compounds and medical devices activated with a solvophobic material functionalized with a first reactive member and methods of making such compounds and devices.

19 Claims, 5 Drawing Sheets

(56) References Cited

U.S. PATENT DOCUMENTS

| | | | |
|---|---|---|---|
| 7,807,619 B2 | 10/2010 | Bertozzi et al. | |
| 7,981,444 B2 | 7/2011 | Tomalia et al. | |
| 7,985,424 B2 | 7/2011 | Tomalia et al. | |
| 8,034,396 B2 | 10/2011 | Kapiamba et al. | |
| 8,969,473 B2 | 3/2015 | Ladet et al. | |
| 2002/0016003 A1 | 2/2002 | Saxon et al. | |
| 2002/0161170 A1 | 10/2002 | Matsuda et al. | |
| 2002/0169275 A1 | 11/2002 | Matsuda et al. | |
| 2002/0173616 A1 | 11/2002 | Matsuda et al. | |
| 2003/0100086 A1 | 5/2003 | Yao et al. | |
| 2003/0135238 A1 | 7/2003 | Milbocker | |
| 2003/0162903 A1 | 8/2003 | Day | |
| 2003/0163198 A1 | 8/2003 | Morra et al. | |
| 2003/0199084 A1 | 10/2003 | Saxon et al. | |
| 2003/0205454 A1 | 11/2003 | Hlavinka et al. | |
| 2004/0170752 A1 | 9/2004 | Luthra et al. | |
| 2004/0185053 A1 | 9/2004 | Govindan | |
| 2004/0209317 A1 | 10/2004 | Ting | |
| 2004/0249438 A1 | 12/2004 | Lefranc et al. | |
| 2005/0032081 A1 | 2/2005 | Ju et al. | |
| 2005/0038472 A1 | 2/2005 | Furst | |
| 2005/0148032 A1 | 7/2005 | Saxon et al. | |
| 2005/0222427 A1 | 10/2005 | Sharpless et al. | |
| 2005/0233389 A1 | 10/2005 | Ting et al. | |
| 2005/0244453 A1 | 11/2005 | Stucke et al. | |
| 2006/0018948 A1 | 1/2006 | Guire et al. | |
| 2006/0036022 A1 | 2/2006 | Callaghan et al. | |
| 2006/0085033 A1 | 4/2006 | Criscuolo et al. | |
| 2006/0108393 A1 | 5/2006 | Heinrich et al. | |
| 2006/0110782 A1 | 5/2006 | Bertozzi et al. | |
| 2006/0142404 A1 | 6/2006 | Berge et al. | |
| 2006/0147963 A1 | 7/2006 | Barone et al. | |
| 2006/0193865 A1 | 8/2006 | Govindan | |
| 2006/0193885 A1* | 8/2006 | Leonard Neethling et al. | 424/422 |
| 2006/0228300 A1 | 10/2006 | Chang et al. | |
| 2006/0228357 A1 | 10/2006 | Chang et al. | |
| 2006/0240092 A1 | 10/2006 | Breitenkamp et al. | |
| 2006/0276658 A1 | 12/2006 | Saxon et al. | |
| 2007/0020620 A1 | 1/2007 | Finn et al. | |
| 2007/0037964 A1 | 2/2007 | Saxon et al. | |
| 2007/0060658 A1 | 3/2007 | Diaz et al. | |
| 2007/0077564 A1 | 4/2007 | Roitman et al. | |
| 2007/0078197 A1* | 4/2007 | Samuelsen | 523/111 |
| 2007/0086942 A1 | 4/2007 | Chang et al. | |
| 2007/0087001 A1 | 4/2007 | Taylor et al. | |
| 2007/0099251 A1 | 5/2007 | Zhang et al. | |
| 2007/0140966 A1 | 6/2007 | Chang et al. | |
| 2007/0178133 A1 | 8/2007 | Rolland | |
| 2007/0178448 A1 | 8/2007 | Tsao et al. | |
| 2007/0190597 A1 | 8/2007 | Agnew et al. | |
| 2007/0212267 A1 | 9/2007 | Organ et al. | |
| 2007/0244265 A1 | 10/2007 | Matyjaszewski et al. | |
| 2007/0244296 A1 | 10/2007 | Tomalia et al. | |
| 2007/0249014 A1 | 10/2007 | Agnew et al. | |
| 2007/0254006 A1 | 11/2007 | Loose et al. | |
| 2007/0258889 A1 | 11/2007 | Douglas et al. | |
| 2007/0269369 A1 | 11/2007 | Gegg et al. | |
| 2007/0272122 A1 | 11/2007 | Lahann et al. | |
| 2007/0275387 A1 | 11/2007 | Ju | |
| 2007/0298006 A1 | 12/2007 | Tomalia et al. | |
| 2008/0015138 A1 | 1/2008 | Hamilton et al. | |
| 2008/0021486 A1 | 1/2008 | Oyola et al. | |
| 2008/0035243 A1 | 2/2008 | Breitenkamp et al. | |
| 2008/0038472 A1 | 2/2008 | Suzuki et al. | |
| 2008/0045686 A1 | 2/2008 | Meagher et al. | |
| 2008/0050731 A1 | 2/2008 | Agnew et al. | |
| 2008/0051562 A1 | 2/2008 | Chaikof et al. | |
| 2008/0103564 A1 | 5/2008 | Burkinshaw et al. | |
| 2008/0121657 A1 | 5/2008 | Voegele et al. | |
| 2008/0138317 A1 | 6/2008 | Fung | |
| 2008/0160017 A1 | 7/2008 | Baker et al. | |
| 2008/0166363 A1 | 7/2008 | Govindan et al. | |
| 2008/0171067 A1 | 7/2008 | Govindan et al. | |
| 2008/0187956 A1 | 8/2008 | Carrico et al. | |
| 2008/0199736 A1 | 8/2008 | Gadeken et al. | |
| 2008/0200628 A1 | 8/2008 | Gadeken et al. | |
| 2008/0207913 A1 | 8/2008 | Breitenkamp et al. | |
| 2008/0214436 A1 | 9/2008 | Yu et al. | |
| 2008/0214801 A1 | 9/2008 | Saxon et al. | |
| 2008/0214831 A1 | 9/2008 | Sharpless et al. | |
| 2008/0221043 A1 | 9/2008 | Harth et al. | |
| 2008/0241856 A1 | 10/2008 | Wong et al. | |
| 2008/0241892 A1 | 10/2008 | Roitman et al. | |
| 2008/0242171 A1 | 10/2008 | Huang et al. | |
| 2008/0248126 A1 | 10/2008 | Cheng et al. | |
| 2008/0267878 A1 | 10/2008 | Robillard et al. | |
| 2008/0283572 A1 | 11/2008 | Boyden et al. | |
| 2008/0311412 A1 | 12/2008 | Fokin et al. | |
| 2008/0317861 A1 | 12/2008 | Guan | |
| 2009/0012457 A1 | 1/2009 | Childers et al. | |
| 2009/0018646 A1 | 1/2009 | Zhao | |
| 2009/0027603 A1 | 1/2009 | Samulski et al. | |
| 2009/0038701 A1 | 2/2009 | Delmotte | |
| 2009/0053139 A1 | 2/2009 | Shi et al. | |
| 2009/0054619 A1 | 2/2009 | Baker et al. | |
| 2009/0061010 A1 | 3/2009 | Zale et al. | |
| 2009/0069561 A1 | 3/2009 | Fokin et al. | |
| 2009/0082224 A1 | 3/2009 | Haddleton et al. | |
| 2009/0099108 A1 | 4/2009 | Jones | |
| 2009/0124534 A1 | 5/2009 | Reineke | |
| 2009/0137424 A1 | 5/2009 | Tsao et al. | |
| 2009/0181402 A1 | 7/2009 | Finn et al. | |
| 2009/0182151 A1 | 7/2009 | Wu et al. | |
| 2009/0202433 A1 | 8/2009 | Chang et al. | |
| 2009/0203131 A1 | 8/2009 | Reineke et al. | |
| 2009/0214755 A1 | 8/2009 | Armani et al. | |
| 2009/0220607 A1 | 9/2009 | Kiser et al. | |
| 2009/0240030 A1 | 9/2009 | Ju et al. | |
| 2009/0247651 A1 | 10/2009 | Kapiamba et al. | |
| 2009/0250588 A1 | 10/2009 | Robeson et al. | |
| 2009/0253609 A1 | 10/2009 | Fleury et al. | |
| 2009/0259016 A1 | 10/2009 | Johnson et al. | |
| 2009/0263468 A1 | 10/2009 | McAnulty et al. | |
| 2009/0269277 A1 | 10/2009 | Chang et al. | |
| 2009/0281250 A1 | 11/2009 | DeSimone et al. | |
| 2009/0297609 A1 | 12/2009 | Shoichet et al. | |
| 2009/0306310 A1 | 12/2009 | Wu et al. | |
| 2009/0312363 A1 | 12/2009 | Bradner et al. | |
| 2009/0325292 A1 | 12/2009 | Baker et al. | |
| 2010/0011472 A1 | 1/2010 | Hugel et al. | |
| 2010/0015046 A1 | 1/2010 | Govindan et al. | |
| 2010/0021391 A1 | 1/2010 | Douglas et al. | |
| 2010/0034862 A1 | 2/2010 | Laronde et al. | |
| 2010/0047258 A1 | 2/2010 | Wang et al. | |
| 2010/0048738 A1 | 2/2010 | Fleury et al. | |
| 2010/0069578 A1 | 3/2010 | Faust et al. | |
| 2010/0098640 A1 | 4/2010 | Cohen et al. | |
| 2010/0104589 A1 | 4/2010 | Govindan et al. | |
| 2010/0121022 A1 | 5/2010 | Musa et al. | |
| 2010/0159508 A1 | 6/2010 | Yang et al. | |
| 2010/0247433 A1 | 9/2010 | Tirrell et al. | |
| 2010/0286405 A1 | 11/2010 | Fokin et al. | |
| 2010/0291171 A1 | 11/2010 | Crescenzi et al. | |
| 2010/0303754 A1 | 12/2010 | Turpin et al. | |
| 2011/0008251 A1 | 1/2011 | Chang et al. | |
| 2011/0052696 A1 | 3/2011 | Hult et al. | |
| 2011/0060107 A1 | 3/2011 | Matyjaszewski et al. | |
| 2011/0143435 A1 | 6/2011 | Stayton et al. | |
| 2011/0177156 A1 | 7/2011 | Szoka, Jr. et al. | |
| 2011/0183417 A1 | 7/2011 | Reineke | |
| 2011/0213123 A1 | 9/2011 | Bertozzi et al. | |

FOREIGN PATENT DOCUMENTS

| | | |
|---|---|---|
| EP | 1790702 A1 | 5/2007 |
| EP | 1795563 A1 | 6/2007 |
| EP | 1975230 A1 | 10/2008 |
| EP | 2014308 A2 | 1/2009 |
| EP | 2090592 A1 | 8/2009 |
| WO | 2004075943 | 9/2004 |
| WO | 2006012569 A1 | 2/2006 |
| WO | 2007003054 A1 | 1/2007 |
| WO | 2007041394 A2 | 4/2007 |

(56) References Cited

FOREIGN PATENT DOCUMENTS

| WO | 2007121055 A1 | 10/2007 |
|---|---|---|
| WO | 2008013618 A1 | 1/2008 |
| WO | 2008075955 A2 | 6/2008 |
| WO | 2008077406 A2 | 7/2008 |
| WO | 2008108736 A1 | 9/2008 |
| WO | 2008115694 A2 | 9/2008 |
| WO | 2008120016 A1 | 10/2008 |
| WO | 2010095049 A1 | 8/2010 |

OTHER PUBLICATIONS

Zhang, et al., "2-Azido-2-deoxycellulose: Synthesis and 1, 3-Dipolar Cycloaddition", Helvetica Chimica Acta, vol. 91, pp. 608-617 (2008).

R. Riva, et al., "Contribution of "Click Chemistry" to the Synthesis of Antimicrobial Aliphatic Copolyester", Polymer 49, (2008), pp. 2023-2028.

Baskin, et al., "Copper Free Click Chemistry for Dynamic In Vivo Imaging", PNAS, vol. 104, No. 43, (Oct. 23, 2007), pp. 16793-16797.

Codelli, et al., "Second Generation Difluorinated Cyclooctynes for Copper-Free Click Chemistry", J. Am. Chem. Soc., vol. 130, No. 34, (2008), pp. 11486-11493.

Sletten and Bertozzi, "A Hydrophilic Azacyclooctyne for Cu-free Click Chemistry", Org. Lett. (2008) 10(14), pp. 3097-3099.

Cazalis, et al. "C-Terminal Site-Specific PEGylation of a Truncated Thrombomodulin Mutant with Retention of Full Bioactivity", Bioconjugate Chem., (2004), 15, pp. 1005-1009.

Haridas, et al., "Design and Synthesis of Triazole-based Peptidedendrimers" Tetrahedron Letters, vol. 48, (2007), pp. 4719-4722.

Raghavan, et al., "Chemical Probes for Profiling Fatty Acid-associated Proteins in Living Cells", Bioorg. Med. Chem. Lett., 18 (2008), pp. 5982-5986.

LeDevedec, et al., "Separation of Chitosan Oligomers by Immobilized Metal Affinity Chromatography", Journal of Chromatography A., 2008, 1194(2), pp. 165-171.

Hartgerink, et al., "Peptide-amphiphile Nanofibers: A Versatile Scaffold for the Preparation of Self Assembling Materials", PNAS, 2002; 99(2), pp. 5133-5138.

Van Berkel, et al., "Metal-Free Triazole Formation as a Tool for Bioconjugation" Chem Bio Chem, 8, (2007), pp. 1504-1508.

Nottelet, et al., Synthesis of an X-ray opaque biodegradable copolyester by chemical modification of poly (.epsilon.-caprolactone) Biomaterials, 27, (2006), pp. 4943-4954.

Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.

Skierka, et al., "The Influence of Different Acids and Pepsin on the Extractability of Collagen From the Skin of Baltic Cod (*Gadus morhua*)", Food Chemisty, 105, (2007), pp. 1302-1306.

Eastoe, "The Amino Acid Composition of Mammalian Collagen and Gelatin", vol. 61, (1955), pp. 589-600.

Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.

Laughlin, et al., "In Vivo Imaging of Membrane-Associated Glycans in Developing Zebrafish", Science, 320, (2008), pp. 664-667.

Worch and Wittmann, "Unexpected Formation of Complex Bridged Tetrazoles via Intramolecular 1,3-dipolar Cycloaddition of 1,2-0-cyanoallcylidene Derivatives of 3-azido-3-deoxy-D-allose", Carbohydrate Research, 343, (2008), pp. 2118-2129.

Witczak et al., "A Click Chemistry Approach to Glycomimetics: Michael addition of 2,3,4,6-tetra-O-acetyl-1-thio-.beta.-D-glucopyranose to 4-deoxy-1,2-O-isopropylident-L-glycero-pent-4-enopyranos-3-ulose-a convenient route to novel4-deoxy-(1.fwdarw.,5)-5-C-thiodisaccharides", Carbohydrate Research, 342, (2007), 1929-1933.

Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461.

Srinivasachari, et al., "Versatile Supramolecular pDNA Vehicles via "Click Polymerization" of .beta.-cyclodextrin with oligoethyleneamines", Biomaterials, 30, (2009), pp. 928-938.

Arora, et al., "A Novel domino-click approach for the synthesis of sugar based unsymmetrical bis-1,2,3-triazoles", Carbohydrate Research, 343, (2008), 139-144.

Chen, et al., "Synthesis of a C.sub.3-symmetric (1.fwdarw.6)-N-acetyl-.beta.-D-glucosamine Octadecasaccharide using Click Chemistry", Carbohydrate Research, 340, (2005), pp. 2476-2482.

Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.

Srinivasachari, etal., "Effects of Trehalose Click Polymer Length on pDNA Complex Stability and Delivery Efficacy", Biomaterials, 28, (2007), pp. 2885-2898.

Godeau, et al., "Lipid-Conjugated Oligonucleotides via Click Chemistry" Efficiently Inhibit Hepatitis C Virus Translation, J. med. Chem., 2008, 51(15), pp. 2374-4376.

Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.

Cantel, et al., "Synthesis and Conformational Analysis of a Cyclic Peptide Obtained via i to i + 4 Intramolecular Side-chain to Side-chain Azide-Alkyne 1,3-Dipolar Cycloaddition" J. Org. Chem., 2008, 73 (15), pp. 5663-5614.

Dijk, et al., "Synthesis of Peptide-Based Polymers by Microwave-Assisted Cycloaddition Backbone Polymerization," Biomacro molecules, 2007, 8(2), pp. 327-330.

Koster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332.

Dijk, et al., "Synthesis and Characterization of Biodegradable Peptide-Baed Polymers Prepared by Microwave-Assisted Click Chemisty", Biomacromolecules, 2008, 9(10), pp. 2834-2843.

Jiang, et al., "Amphiphilic PEG/alkyl-grafted comb polylactides", J. Polymer Science Part B: Polymer Physics, 45(22), 2007, pp. 5227-5236.

Ochs, et al., "Low-Fouling, Biofunctionalized, and Biodegradable Click Capsules", Biomacromolecules, 2008, 9(12), pp. 3389-3396.

Beatty and Tirrell, "Two-color Labeling of Temporally Defined Protein Populations in Mammalian Cells", Bioorg. Med. Chem. Lett., 18 (2008), pp. 5995-5999.

Kolb, et al., "Click Chemistry: Diverse Chemical Function from a Few Good Reactions", Angewandte Chemie, International Edition, Jun. 2001, pp. 2004-2021.

Krouit, et al., "Cellulose surface grafting with polycaprolactone by heterogeneous click-chemistry", European Polymer Journal 44, Dec. 2008, pp. 4074-4081.

Nandivada, et al. "Reactive polymer coatings that 'Click'.", Angewandte Chemie, International Edition 45, Apr. 2006, pp. 3360-3363.

Ossipov and Hilborn, "Poly(vinyl alcohol)-Based Hydrogels Formed by Click Chemistry", Macromelecules 2006, 39, pp. 1709-1718.

Binder and Sachsenhofer, "Click Chemistry in Polymer and Materials Science", Macromolecular Rapid Commun. 2007, 28, pp. 15-54.

\* cited by examiner

COMPOUNDS AND MEDICAL DEVICES
ACTIVATED WITH SOLVOPHOBIC LINKERS

CROSS REFERENCE TO RELATED APPLICATIONS

This application is a divisional of U.S. patent application Ser. No. 13/202,366 filed Oct. 13, 2011, now U.S. Pat. No. 8,969,473, which is a National Stage Application of PCT/IB10/000630 filed Feb. 22, 2010, which claims the benefit of U.S. Provisional Application No. 61/154,374 filed Feb. 21, 2009, and the disclosures of each of the above-identified applications are hereby incorporated by reference in their entirety.

BACKGROUND

1. Technical Field

The present disclosure relates to functionalized compounds having solvophilic and solvophobic portions and to activated medical devices made with such compounds.

2. Background of Related Art

The systemic administration of bioactive agents, such as by intravenous means, treats the body as a whole even though the disease to be treated is often localized. Thus, efforts have recently been made to develop medical devices having a bioactive agent bound to the medical devices, to deliver the bioactive agent directly to the area of localization when the medical device in implanted. However, the development of such medical devices is highly complex and is often limited in practice by number of practical reactions available to combine the medical device with the agents, as well as the resultant by-products of the device upon degradation of the device in the body.

Accordingly, it would be beneficial to provide a compound or medical device which does not require any complex reaction schemes or cross-linking reactions but rather requires the simple combination or blending of ingredients to produce an activated compound or medical device capable of easily attaching to a bioactive agent.

SUMMARY

Compounds described herein include a solvophilic portion and a solvophobic portion where the solvophobic portion is functionalized with one or more first reactive members.

By "reactive member" is meant, according to the present application any reactive member of functional group capable of interacting with another reactive member, in other words a complementary reactive member, in order to form covalent bonds. In the present application, the terms "reactive member", functional group" are used interchangeably. In the present application, the first reactive member and the second reactive member are able to interact with one another form covalent bonds.

The first reactive members of the activated compounds may provide for the covalent attachment of a variety of materials, such as, for example, bioactive agents functionalized with reactive members, also called second reactive members, that are complementary to the first reactive members.

Medical devices containing such activated compounds are also described herein. By "activated" or "functionalized" compound or medical device, is meant, according to the present application, a compound or medical device functionalized by, in other words with, a reactive member. The medical devices combine an activated compound with a solvent matrix. The activated compound includes a solvophilic portion that is relatively compatible with the solvent matrix and a solvophobic portion that is relatively incompatible with the solvent matrix and therefore remains at or near the surface of the device. Because the solvophobic portion is functionalized with a first reactive member, the reactive member is also positioned at or near the surface of the solvent matrix, thereby creating a medical device having an activated surface.

Methods for forming such compounds and devices are also described.

A first aspect of the invention is a compound comprising:
a solvophilic material and a solvophobic material, the solvophobic material being functionalized with a first reactive member.

Another aspect of the invention is a method of forming an activated medical device comprising:
preparing a composition by combining a solvent matrix with a compound which includes a solvophilic material and a solvophobic material, the solvophobic material being functionalized with a first reactive member, and
forming at least a portion of a medical device from the composition.

Another aspect of the invention is a medical device comprising
a solvent matrix and a compound including a solvophobic material and a solvophilic material, the solvophobic material being functionalized with a first reactive member,
wherein the solvophilic material is positioned within the solvent matrix and the solvophobic material including the reactive member is positioned outside the solvent matrix.

In embodiments, the first reactive member is an electrophilic group. In alternative embodiments, the first reactive member is a nucleophilic group. In alternative embodiments, the first reactive member is an alkyne group. In alternative embodiments, the first reactive member is an azide group.

In embodiments, the solvent matrix is selected from the group consisting in a solid, a gel and a liquid.

In embodiments, the solvent matrix is hydrophilic. In such embodiments, the solvophilic material may include polyamides, hydrophilic polyurethanes, polylactones, polyimides, polylactams, poly-vinyl-pyrrolidone, polyvinyl alcohols, polyacrylic acid, polymethacrylic acid, poly(hydroxyethyl methacrylate), gelatin, dextan, oligosaccharides, such as chitosan, hyaluronic acid, alginate, chondroitin, mixtures and combinations thereof. The solvophobic material may therefore include polyethylene, polypropylene, hydrophobic polyurethanes, polyacrylates, polymethacrylates, fluoropolymers, polycaprolactone, polylactide, polyglycolide, phospholipids, and polyureas, poly(ethylene/-vinyl acetate), polyvinylchloride, polyesters, polyamides, polycarbonate, polystyrenes, polytetrafluoroethylene, silicones, siloxanes, fatty acids, and chitosan having high degrees of acetylation and mixtures and combinations thereof.

In embodiments, the medical device further comprises a bioactive agent functionalized with a second reactive member, said bioactive agent being covalently bound to said solvophobic material by means of said first reactive member covalently bonding with said second reactive member.

For example, when the first reactive member is an alkyne group, the second reactive member may be an azide group.

Alternatively, when the first reactive member is an azide group, the second reactive member may be an alkyne group. In another embodiment, the first reactive member is an azide group and the second reactive member is an alkene group.

In alternative embodiments, the first reactive member is an electrophilic group and the second reactive member is a nucleophilic group. Alternatively, when the first reactive member is a nucleophilic group, the second reactive member may be an electrophilic group.

DETAILED DESCRIPTION OF PREFERRED EMBODIMENTS

Figure 1:
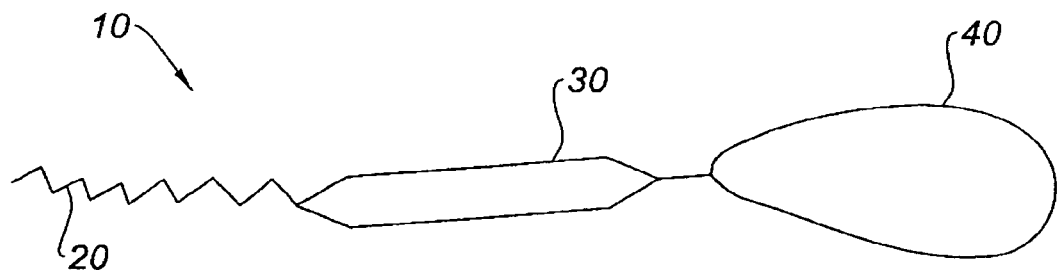
FIG. 1 schematically illustrates an embodiment described herein of an activated compound.

As shown in FIG. 1 and in accordance with the present disclosure, activated compound 10 includes solvophilic portion 20 and solvophobic portion 30 wherein solvophobic portion 30 is functionalized with first reactive member 40. Solvophobic portion 30 and solvophilic portion 20 are covalently bonded to one another. First reactive member 40 provides a site for attachment of another compound (not shown in FIG. 1), such as, for example, a bioactive agent functionalized with a second reactive member which is complementary to the first reactive member of the activated compound.

The activated compounds may be combined with a solvent matrix to form activated implantable medical devices. The medical devices described herein include a solvent matrix and an activated compound which includes a solvophilic portion and a solvophobic portion. When combined, the solvophilic portion of the activated compound is positioned within the solvent matrix and at least a portion of the solvophobic portion, which is functionalized with a first reactive member, is positioned outside, at or near the surface of the solvent matrix.

Figure 2:
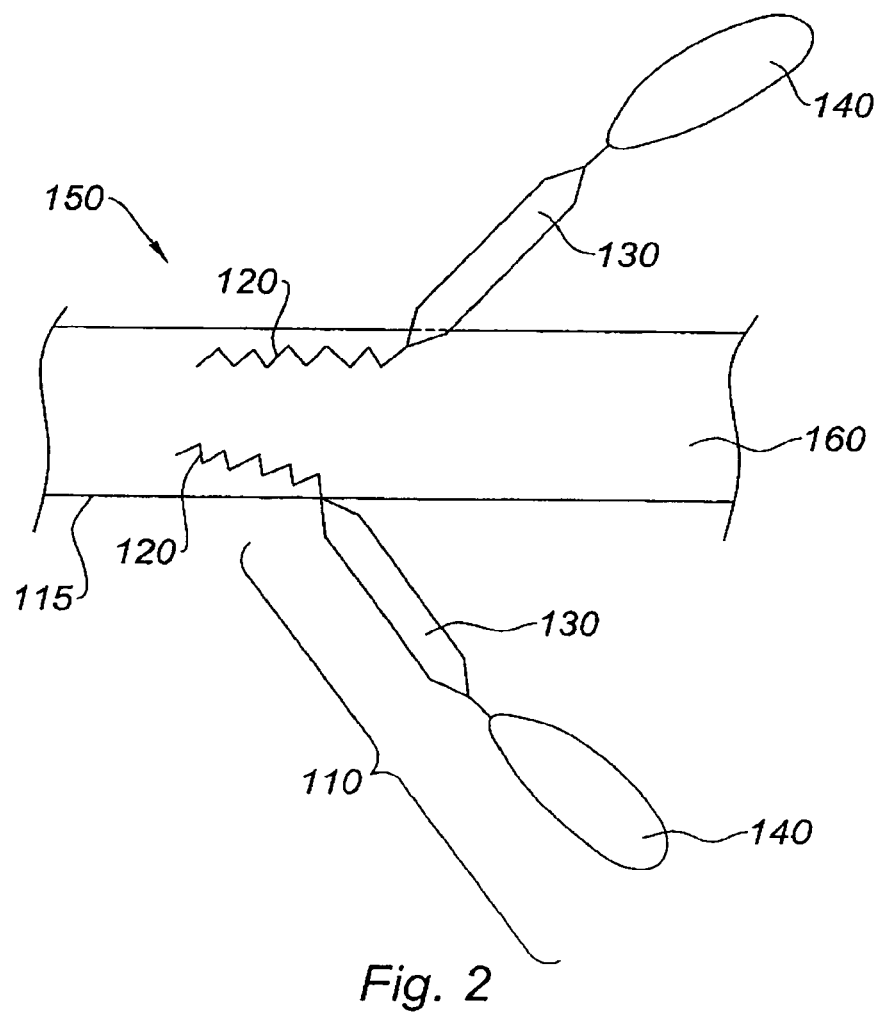
FIG. 2 schematically illustrates embodiments described herein of an activated medical device.

Turning now to FIG. 2, medical device 150, shown as a single fiber or monofilament 115, includes solvent matrix 160 and activated compound 110 which includes solvophilic portion 120 and solvophobic portion 130 with solvophobic portion 130 being functionalized with first reactive member 140. Solvophilic portion 120 is positioned closer in proximity to solvent matrix 160 than solvophobic portion 130. Solvophobic portion 130, which is not attracted to and relatively incompatible with solvent matrix 160, is positioned outside or at the surface of solvent matrix 160, along with first reactive member 140.

Figure 3:
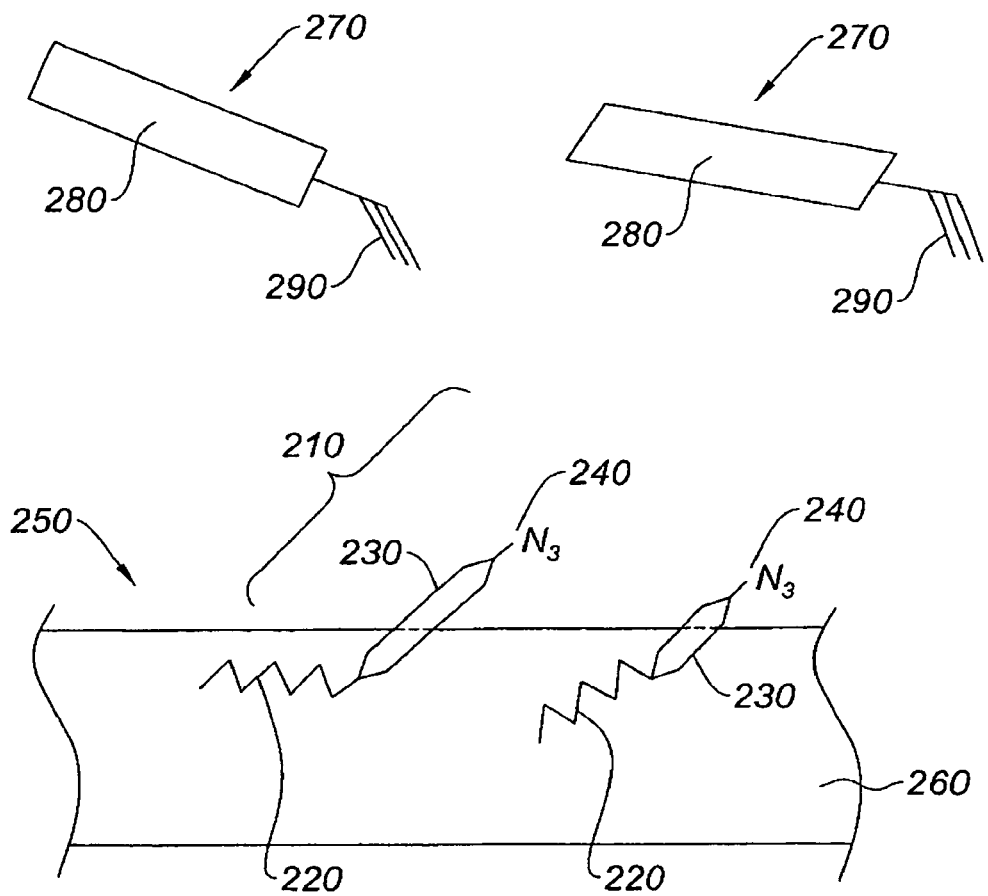
FIGS. 3 and 4 schematically illustrate the formation of a medical device in accordance with the present disclosure.

As shown in FIG. 3, medical device 250 includes solvent matrix 260 and activated compound 210. Activated compound 210 includes first reactive member 240 (in this illustrative example an azide group) positioned on solvophobic portion 230 and solvophilic portion 220 which, due to its compatibility with solvent matrix 260, remains substantially within solvent matrix 260. A compound 270 to be covalently bound to device 250 includes bioactive agent 280 that is functionalized with second reactive member 290. Second reactive member 290 (in this illustrative example an alkyne group) is complementary to first reactive member 240.

Figure 4:
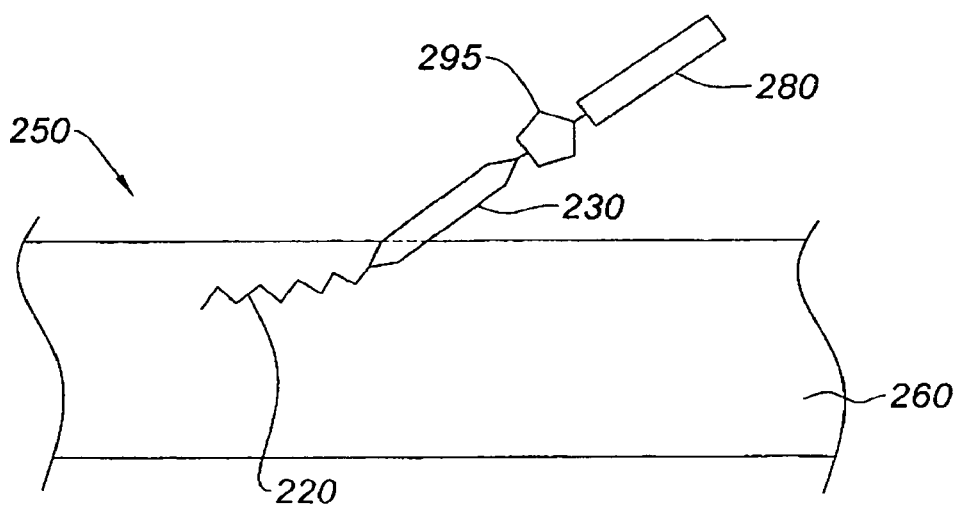

As shown in FIG. 4, bioactive agent 280 is covalently attached to medical device 210 via linkage 295 following the interaction between the first reactive member positioned on the solvophobic portion of the activated compound and the second reactive member on the bioactive agent. In this illustrative example, where the first reactive member is an azide and the second reactive member is alkyne, linkage 295 is a triazole structure.

The Solvent Matrix

The solvent matrix is any material that can form a portion of a medical device. For example, the solvent matrix may form the entire device, a portion of the device, a coating on the device or may be contained within a reservoir of the device. In embodiments, the solvent matrix is a solid. In other embodiments, the solvent matrix is a gel.

It is also contemplated that the solvent matrix could, at the time of incorporation of the activated compound, be a liquid. Thus, for example, in embodiments the solvent matrix may be a solution of a polymer at the time the activated compound is incorporated therein. Due to the mobile nature of the activated compound in the solution, the solvophobic portion of the activated compound migrates to the surface of the solution. Upon evaporation of the solvent, a solid polymer remains having the solvophobic portion at or outside the surface of the solid.

In other embodiments, the solvent matrix can be a melt of one or more polymers into which the activated compound is added. Due to the reduced viscosity of the melt, the solvophobic portion of the activated compound will migrate to the surface of the melt. Upon cooling, the solvophobic portion will be locked at or near the surface of the solidified polymer composition.

In embodiments, the solvent matrix of the medical devices described herein may include any biodegradable polymer. The biodegradable polymer may be a homopolymer or a copolymer, including random copolymer, block copolymer, or graft copolymer. The biodegradable polymer may be a linear polymer, a branched polymer, or a dendrimer. The biodegradable polymers may be of natural or synthetic origin. Examples of suitable biodegradable polymers include, but are not limited to polymers such as those made from lactide, glycolide, caprolactone, valerolactone, carbonates (e.g., trimethylene carbonate, tetramethylene carbonate, and the like), dioxanones (e.g., 1,4-dioxanone), δ-valerolactone, 1,dioxepanones (e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, poly (ortho esters), hydroxy alkanoates, tyrosine carbonates, polyimide carbonates, polyimino carbonates such as poly (bisphenol A-iminocarbonate) and poly (hydroquinone-iminocarbonate), polyurethanes, polyanhydrides, polymer drugs (e.g., polydiflunisol, polyaspirin, and protein therapeutics) and copolymers and combinations thereof. Suitable natural biodegradable polymers include those made from collagen, chitin, chitosan, cellulose, poly (amino acids), polysaccharides, hyaluronic acid, gut, copolymers and derivatives and combinations thereof.

Suitable non-biodegradable materials which may be used as part of the solvent matrix include fluorinated polymers (e.g., fluoroethylenes, propylenes, fluoroPEGs), polyolefins such as polyethylene, polyesters such as poly ethylene terepththalate (PET), nylons, polyamides, polyurethanes, silicones, ultra high molecular weight polyethylene (UHMWPE), polybutesters, polyaryletherketone, copolymers and combinations thereof.

Additionally, non-biodegradable polymers and monomers may be combined with each other and may also be combined with various biodegradable polymers and monomers to create a solvent matrix.

As noted above, at the time of incorporation of the activated compound, the solvent matrix may take the form of any solution, suspension, semi-solid, or solid material capable of allowing the two components to be combined and for the activated compound to migrate toward the surface of the solvent matrix. Thus, in embodiments, the solvent matrix may, in addition to the polymers identified above, may include one or more solvents. Suitable solvents include any solvent capable of dissolving or suspending the polymer used. Suitable solvents which may be utilized include, for example, polar solvents such as water, ethanol, triethylene glycol, dimethyl sulfoxide, glymes (such as diglyme, triglyme, tetraglyme, and the like), polyethylene glycols, methoxy-polyethylene glycols, dimethylformamide, dimethylacetamide, gamma-butyrolactone, n-methylpyrollidone, ketones such as methyl ethyl ketone, cyclohexanone, diethylene glycol momethyl ether acetate, diethylene glycol monobutyl ether acetate, diethylene glycol monomethyl ether, diethylene glycol monoethyl ether, diethylene glycol monobutyl ether, diethylene glycol monoisobutyl either, diisobutyl ketone, diacetone alcohol, ethyl amyl ketone, ethyl lactate, and the like. In other embodiments, solvents such as tetrahydrofuran, ethyl acetate, isopropyl acetate, butyl acetate, isopropanol, butanol, acetone, and the like, may be utilized. In embodiments, combinations of any of the foregoing solvents may be utilized to disperse or dissolve the polymer(s). The amount of solvent used will depend on a number of factors, including the particular polymer or combination of polymers to be employed and the intended end use of the composition.

Other suitable non-limiting solvents include aromatic hydrocarbons, such as toluene, petroleum naphtha or xylenes; nitro paraffins, such as 1-nitropropane and 2-nitropropane, ketones such as, methyl amyl ketone, methyl isobutyl ketone, methyl ethyl ketone or acetone; esters such as, butyl acetate or hexyl acetate; and glycol ether esters $C_1$ to $C_{12}$ mono and di-alcohols, such as, for example, isopropanol, ethanol, methanol, butanol, isobutanol, acetone, diacetone alcohol, 2-ethylhexanol and dodecanol; tetrahydrofuran, glycol ethers and glycol ether acetates such as, propylene glycol monomethyl ether acetate; toluene; benzene; xylene; chlorinated aliphatic solvents; hexane; butyl cellosolve; butyl cellosolve acetate; methyl amyl alcohol, cyclohexanone, primary amyl acetate, methyl amyl ketone, 2-ethyl hexanol, propanol, ethyl acetate, tetrahydrofuran, isopropyl acetate, 2-ethyl hexyl acetate, ethyl 3-ethoxy propionate, pentyl propionate, ethanol, n-butyl propionate, tertiary butyl alcohol and 1-pentanol and carbitol.

The Activated Compounds

The activated compounds include at least one portion which is solvophilic and at least one portion which is solvophobic. The term "solvophilic" is generally defined in terms of being miscible, compatible, or attracted to, a given solvent matrix. The term "solvophobic" is generally defined in terms of being immiscible, incompatible, or not attracted to a given solvent matrix. As described below, a variety of different solvent matrix materials may be combined with the activated compounds to form the medical devices described herein, thus a given material may be either solvophobic or solvophilic depending upon the solvent matrix. The activated compounds may be linear, branched, block or graft copolymers.

As noted above, in embodiments the solvent matrix can simply be a molten polymer or combination of polymers. In such embodiments, the activated compound may include a solvophilic portion that is an oligomer of the molten polymer. The solvophobic portion of the compound would be selected from materials that are immiscible, incompatible, or not attracted to the molten polymer(s).

In embodiments wherein the solvent matrix is hydrophilic in nature, the solvophilic portions may be derived from hydrophilic polymers or compounds. Suitable hydrophilic materials which may make up the solvophilic portion of the compound include polyamides, hydrophilic polyurethanes, polylactones, polyimides, polylactams, poly-vinyl-pyrrolidone, polyvinyl alcohols, polyacrylic acid, polymethacrylic acid, poly(hydroxyethyl methacrylate), gelatin, dextan, oligosaccharides, such as chitosan, hyaluronic acid, alginate, chondroitin, mixtures and combinations thereof. In such embodiments, the solvophobic materials may be derived from hydrophobic polymers or compounds selected from the group consisting of polyethylene, polypropylene, hydrophobic polyurethanes, polyacrylates, polymethacrylates, fluoropolymers, polycaprolactone, polylactide, polyglycolide, phospholipids, and polyureas, poly(ethylene/-vinyl acetate), polyvinylchloride, polyesters, polyamides, polycarbonate, polystyrenes, polytetrafluoroethylene, silicones, siloxanes, fatty acids, and chitosan having high degrees of acetylation and mixtures and combinations thereof. The activated compounds may include any biocompatible combination of solvophilic and solvophobic materials.

In embodiments, the activated compound may include a solvophobic material derived from a fatty acid, some non-limiting examples include saturated fatty acids, monoenoic fatty acids, polyenoic fatty acids, methylene-interrupted polymethylene-interrupted, conjugated, allenic acids, cumulenic acids, acetylenic fatty acids, hydroxy fatty acids, dicarboxylic acids, fatty acid carbonates, divinyl ether fatty acids, sulfur containing fatty acids, fatty acid amides, methoxy and acetoxy fatty acids, keto fatty acids, aldehydic fatty acids, halogenated fatty acids (F, Cl, Br), nitrated fatty acids, arsenic containing fatty acids, branched-chain fatty acids, mono or multibranched chain fatty acids, branched methoxy fatty acids, branched hydroxy fatty acids, ring containing fatty acids, cyclopropane acids, cyclobutane acids, cyclopentenyl acids, furanoid acids, cyclohexyl acids, phenylalkanoic acids, epoxy acids, cyclic fatty peroxides, lipoic acids and combinations thereof. Examples of saturated fatty acids include butanoic, pentanoic, hexanoic, octanoic, nonanoic, decanoic, dodecanoic, tetradecanoic, hexadecanoic, heptadecanoic, octadecanoic, eicosanoic, docosanoic, tetracosanoic, hexacosanoic, heptacosanoic, and octacosanoic. In embodiments, the fatty acid may include one of the following formulas: $C_6H_{11}O$, $C_{10}H_{19}O$, $C_{16}H_{31}O$, $C_{22}H_{43}O$. The activated compound may also includes a solvophilic material derived from an oligosaccharide such as chitosan, hyaluronic acid, alginates or chondroitin sulfate.

Chitosan is a natural polysaccharide comprising copolymers of glucosamine and N-acetylglucosamine, and can be obtained by the partial acetylation of chitin, from crustacean shells, squid pen, and mushrooms the second most abundant natural polymer after cellulose. The process of acetylation involves the removal of acetyl groups from the molecular chain of chitin, leaving behind a complete amino group ($—NH_2$) and chitosan versatility depends mainly on this high degree chemical reactive amino groups. As the degree of acetylation increases, the more hydrophobic the chitosan becomes. Conversely, as the degree of acetylation decreases, the more hydrophilic the chitosan becomes at pH<6. Thus, in some embodiments, chitosan oligmers displaying different degrees of acetylation (and hence different degrees of solvophilicity and solvophobicity) may be combined to form an activated compound. Moreover, in some embodiments in which more than one oligosaccharide may be utilized to form the activated compound, the degree of acetylation of the chitosan oligomers may be altered depending on the solvophilicity of the other oligosaccharides. For instance, the activated compound may include a solvophilic portion derived from a chitosan oligomer having a low degree of acetylation, ranging from about 0 to about 30%, and a solvophobic portion derived from a chitosan oligomer having a higher degree of acetylation, greater than about 50% at a pH<6. Alternatively, the activated compound may be formed under a raised pH (pH>7) such that the compound includes a solvophobic portion derived from a chitosan oligomer having a low degree of acetylation, ranging from about 0 to about 10%, and a solvophilic portion derived from a hyaluronic acid oligomer or alginate oligomer which under the raised pH conditions displays a negative charge. Under the raised pH conditions, the chitosan oligomer having a low degree of acetyltion displays a positive charge and becomes more solvophilic.

In still other embodiments, a fatty acid solvophobic portion may be combined with a solvophilic peptide or drug. Some non-limiting examples of solvophilic polypeptides or drugs include oxytocin, vasopressin, adrenocorticotrophic hormone (ACTH), epidermal growth factor (EGF), transforming growth factor antagonists, prolactin, luliberin or luteinizing hormone releasing hormone (LH-RH), LH-RH agonists or antagonists, growth hormone, growth hormone releasing factor, insulin, somatostatin, bombesin antagonists, glucagon, interferon, gastrin, tetragastrin, pentagastrin, urogastrone, secretin, calcitonin, enkephalins, endorphins, angiotensins, renin, bradykinin, bacitracins, polymyzins, colistins, tyrocidin, gramicidines, and synthetic analogues and modifications and pharmaceutically-active fragments thereof, monoclonal antibodies and soluble vaccines.

Where the solvent matrix is in the form of a solution, suspension or emulsion of a polymer, the solvophilic portion of the compound may be chosen to be miscible, compatible, or attracted to, a solvent used to make the solution, suspension or emulsion and the solvophobic portion of the compound may be chosen to be immiscible, incompatible, or not attracted to a given solvent used to make the solution, suspension or emulsion. For a given solvent matrix, those skilled in the art reading the present disclosure will readily envision suitable solvophilic and solvophobic materials to form the activated compound.

The solvophilic and solvophobic portions of the compound are covalently bound together using techniques within the purview of those skilled in the art.

Functionalizing the Solvophobic Portion of the Compound

In order to activate the compound, the solvophobic portion of the compound is functionalized with a first reactive member. In order to covalently bond another compound (e.g., a bioactive agent) to the solvophobic portion of the activated compound, the solvophobic portion of the activated compound is functionalized with a first reactive member and the other compound is functionalized with a second reactive member that is complementary to the first reactive members. By "complementary" it is meant that the first and second reactive members are able to interact with one another to covalently bond the bioactive agent to the activated compound.

In embodiments, the solvophobic portion of the compound is functionalized with electrophilic or nucleophilic functional groups, such that, for example, a nucleophilic functional group on the solvophobic portion of the activated compound may later be reacted with an electrophilic functional group on another compound (e.g., a different activated compound containing a bioactive agent) to form a covalent bond.

Virtually any nucleophilic group can be used to functionalize the solvophobic portion of the compound. Alternatively, virtually any electrophilic group can be used to functionalize the solvophobic portion to create the activated compound. In embodiments, the reaction occurs without need for ultraviolet or other radiation. In embodiments, the reactions the complementary groups should be complete in under 60 minutes, in embodiments under 30 minutes, in yet other embodiments, the reaction occurs in about 5 to 15 minutes or less.

Non-limiting examples of nucleophilic groups include, but are not limited to, $-NH_2$, $-NHR$, $-N(R)_2$, $-SH$, $-OH$, $-COOH$, $-C_6H_4-OH$, $-PH_2$, $-PHR$, $-P(R)_2$, $-NH-NH_2$, $-CO-NH-NH_2$, $-C_5H_4N$, etc. wherein R is hydrocarbyl, typically $C_1$-$C_4$ alkyl or monocyclic aryl. Organometallic moieties are also useful nucleophilic groups for the purposes of this disclosure, particularly those that act as carbanion donors. Examples of organometallic moieties include: Grignard functionalities $-RMgHal$ wherein R is a carbon atom (substituted or unsubstituted), and Hal is halo, typically bromo, iodo or chloro; and lithium-containing functionalities, typically alkyllithium groups; sodium-containing functionalities.

It will be appreciated by those of ordinary skill in the art that certain nucleophilic groups must be activated with a base so as to be capable of reaction with an electrophile. For example, when there are nucleophilic sulfhydryl and hydroxyl groups on the solvophobic material of the activated compound or activated medical device, the bioactive agent must be admixed with an aqueous base in order to remove a proton and provide an $-S^-$ or $-O^-$ species to enable reaction with an electrophile. Unless it is desirable for the base to participate in the reaction, a non-nucleophilic base is used. In some embodiments, the base may be present as a component of a buffer solution.

The selection of electrophilic groups provided on the compound to be covalently bound to the activated compound is made so that reaction is possible with the specific nucleophilic groups on the solvophobic portion of the activated compound. Thus, when the solvophobic portion of the activated compound is functionalized with amino groups, the compound to be covalently bound to the activated compound is functionalized with groups selected so as to react with amino groups. Analogously, when the solvophobic portion of the activated compound is functionalized with sulhydryl moieties, the corresponding electrophilic groups can be sulfhydryl-reactive members, and the like.

In embodiments, when the solvophobic portion of the activated compound is functionalized with amino groups (generally although not necessarily primary amino groups), the electrophilic groups present on the compound to be covalently bound to the activated compound are amino reactive members such as, but not limited to: (1) carboxylic acid esters, including cyclic esters and "activated" esters; (2) acid chloride groups ($-CO-Cl$); (3) anhydrides ($-(CO)-O-(CO)-R$); (4) ketones and aldehydes, including α,β-unsaturated aldehydes and ketones such as $-CH=CH-CH=O$ and $-CH=CH-C(CH_3)=O$; (5) halides; (6) isocyanate ($-N=C=O$); (7) isothiocyanate ($-N=C=S$); (8) epoxides; (9) activated hydroxyl groups (e.g., activated with conventional activating agents such as carbonyldiimidazole or sulfonyl chloride); and (10) olefins, including conjugated olefins, such as ethenesulfonyl ($-SO_2CH=CH_2$) and analogous functional groups, including acrylate ($-CO_2-C=CH_2$), methacrylate ($-CO_2-C(CH_3)=CH_2$)), ethyl acrylate ($-CO_2-C(CH_2\ CH_3)=CH_2$), and ethyleneimino (—CH=CH—C=NH). Since a carboxylic acid group per se is not susceptible to reaction with a nucleophilic amine, components containing carboxylic acid groups must be activated so as to be amine-reactive. Activation may be accomplished in a variety of ways, but often involves reaction with a suitable hydroxyl-containing compound in the presence of a dehydrating agent such as dicyclohexylcarbodiimide (DCC) or dicyclohexylurea (DHU). For example, a carboxylic acid can be reacted with an alkoxy-substituted N-hydroxy-succinimide or N-hydroxysulfosuccinimide in the presence of DCC to form reactive electrophilic groups, the N-hydroxysuccinimide ester and the N-hydroxysulfosuccinimide ester, respectively. Carboxylic acids may also be activated by reaction with an acyl halide such as an acyl chloride (e.g., acetyl chloride), to provide a reactive anhydride group. In a further example, a carboxylic acid may be converted to an acid chloride group using, e.g., thionyl chloride or an acyl chloride capable of an exchange reaction. Specific reagents and procedures used to carry out such activation reactions will be known to those of ordinary skill in the art and are described in the pertinent texts and literature.

Analogously, when the solvophobic portion of the activated compound is functionalized with sulfhydryl, the electrophilic groups present on the compound to be covalently bound to the activated compound are groups that react with a sulfhydryl moiety. Such reactive members include those that form thioester linkages upon reaction with a sulfhydryl group, such as mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarinide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; and isocyanates. With these sulfhydryl reactive members, auxiliary reagents can also be used to facilitate bond formation, e.g., 1-ethyl-3-[3-dimethylaminopropyl]carbodiimide can be used to facilitate coupling of sulfhydryl groups to carboxyl-containing groups.

In addition to the sulfhydryl reactive members that form thioester linkages, various other sulfydryl reactive functionalities can be utilized that form other types of linkages. For example, compounds that contain methyl imidate derivatives form imido-thioester linkages with sulfhydryl groups. Alternatively, sulfhydryl reactive members can be employed that form disulfide bonds with sulfhydryl groups, such groups generally have the structure —S—S—Ar where Ar is a substituted or unsubstituted nitrogen-containing heteroaromatic moiety or a non-heterocyclic aromatic group substituted with an electron-withdrawing moiety, such that Ar may be, for example, 4-pyridinyl, o-nitrophenyl, m-nitrophenyl, p-nitrophenyl, 2,4-dinitrophenyl, 2-nitro-4-benzoic acid, 2-nitro-4-pyridinyl, etc. In such instances, auxiliary reagents, i.e., mild oxidizing agents such as hydrogen peroxide, can be used to facilitate disulfide bond formation.

Yet another class of sulfhydryl reactive members forms thioether bonds with sulfhydryl groups. Such groups include, inter alfa, maleimido, substituted maleimido, haloalkyl, epoxy, imino, and aziridino, as well as olefins (including conjugated olefins) such as ethenesulfonyl, etheneimino, acrylate, methacrylate, and $\alpha,\beta$-unsaturated aldehydes and ketones.

When the solvophobic portion of the activated compound is functionalized with —OH, the electrophilic functional groups on the compound to be covalently bound to the activated compound are chosen to react with hydroxyl groups. The hydroxyl group may be activated as described above with respect to carboxylic acid groups, or it may react directly in the presence of base with a sufficiently reactive electrophile such as an epoxide group, an aziridine group, an acyl halide, an anhydride, When the solvophobic portion of the activated compound is functionalized with an organometallic nucleophile such as a Grignard functionality or an alkyllithium group, suitable electrophilic functional groups for reaction therewith are those containing carbonyl groups, including, by way of example, ketones and aldehydes.

It will also be appreciated that certain functional groups can react as nucleophiles or as electrophiles, depending on the selected reaction partner and/or the reaction conditions. For example, a carboxylic acid group can act as a nucleophile in the presence of a fairly strong base, but generally acts as an electrophile allowing nucleophilic attack at the carbonyl carbon and concomitant replacement of the hydroxyl group with the incoming nucleophile.

Table 1, below illustrates, solely by way of example, representative complementary pairs of electrophilic and nucleophilic functional groups that may be employed in functionalizing the solvophobic portion of the activated compound (e.g., $R_1$ in Table 1) and the compound to be covalently bound to the activated compound (e.g., $R_2$ in Table 1).

TABLE 1

| REPRESENTATIVE NUCLEOPHILIC COMPONENT (A, $FN_{NU}$) | REPRESENTATIVE ELECTROPHILIC COMPONENT (B, $FN_{EL}$) | RESULTING LINKAGE |
|---|---|---|
| $R^1$—$NH_2$ | $R^2$—O—(CO)—O—N($COCH_2$) (succinimidyl carbonate terminus) | $R^1$—NH—(CO)—O—$R^2$ |
| $R^1$—SH | $R^2$—O—(CO)—O—N($COCH_2$) | $R^1$—S—(CO)—O—$R^2$ |
| $R^1$—OH | $R^2$—O—(CO)—O—N($COCH_2$) | $R^1$—S—(CO)—$R^2$ |
| $R^1$—$NH_2$ | $R^2$—O(CO)—CH=$CH_2$ (acrylate terminus) | $R^1$—NH—$CH_2CH_2$—(CO)—O—$R^2$ |
| $R^1$—SH | $R^2$—O—(CO)—CH=$CH_2$ | $R^1$—S—$CH_2CH_2$—(CO)—O—$R^2$ |
| $R^1$—OH | $R^2$—O—(CO)—CH=$CH_2$ | $R^1$—O—$CH_2CH_2$—(CO)—O—$R^2$ |
| $R^1$—$NH_2$ | $R^2$—O(CO)—$(CH_2)_3$—$CO_2$N($COCH_2$) (succinimidyl glutarate terminus) | $R^1$—NH—(CO)—$(CH_2)_3$—(CO)—$OR^2$ |
| $R^1$—SH | $R^2$—O(CO)—$(CH_2)_3$—$CO_2$—N($COCH_2$) | $R^1$—S—(CO)—$(CH_2)_3$—(CO)—$OR^2$ |
| $R^1$—OH | $R^2$—O(CO)—$(CH_2)_3$—$CO_2$—N($COCH_2$) | $R^1$—O—(CO)—$(CH_2)_3$—(CO)—$OR^2$ |
| $R^1$—$NH_2$ | $R^2$—O—$CH_2$—$CO_2$—N($COCH_2$) (succinimidyl acetate terminus) | $R^1$—NH—(CO)—$CH_2$—$OR^2$ |
| $R^1$—SH | $R^2$—O—$CH_2$—$CO_2$—N($COCH_2$) | $R^1$—S—(CO)—$CH_2$—$OR^2$ |
| $R^1$—OH | $R^2$—O—$CH_2$—$CO_2$—N($COCH_2$) | $R^1$—O—(CO)—$CH_2$—$OR^2$ |

TABLE 1-continued

| REPRESENTATIVE NUCLEOPHILIC COMPONENT (A, $FN_{NU}$) | REPRESENTATIVE ELECTROPHILIC COMPONENT (B, $FN_{EL}$) | RESULTING LINKAGE |
|---|---|---|
| $R^1$—$NH_2$ | $R^2$—O—NH(CO)—$(CH_2)_2$—$CO_2$—N($COCH_2$) (succinimidyl succinamide terminus) | $R^1$—NH—(CO)—$(CH_2)_2$—(CO)—NH—$OR^2$ |
| $R^1$—SH | $R^2$—O—NH(CO)—$(CH_2)_2$—$CO_2$—N($COCH_2$) | $R^1$—S—(CO)—$(CH_2)_2$—(CO)—NH—$OR^2$ |
| $R^1$—OH | $R^2$—O—NH(CO)—$(CH_2)_2$—$CO_2$—N($COCH_2$) | $R^1$—O—(CO)—$(CH_2)_2$—(CO)—NH—$OR^2$ |
| $R^1$—$NH_2$ | $R^2$—O—$(CH_2)_2$—CHO (propionaldehyde terminus) | $R^1$—NH—(CO)—$(CH_2)_2$—$OR^2$ |
| $R^1$—$NH_2$ | $R^2$—O—$CH_2$—CH—$CH_2$ (epoxide, glycidyl ether terminus) | $R^1$—NH—$CH_2$—CH(OH)—$CH_2$—$OR^2$ and $R^1$—N[$CH_2$—CH(OH)—$CH_2$—$OR^2$]$_2$ |
| $R^1$—$NH_2$ | $R^2$—O—$(CH_2)_2$—N=C=O (isocyanate terminus) | $R^1$—NH—(CO)—NH—$CH_2$—$OR^2$ |
| $R^1$—$NH_2$ | $R^2$—$SO_2$—CH=$CH_2$ (vinyl sulfone terminus) | $R^1$—NH—$CH_2CH_2$—$SO_2$—$R^2$ |
| $R^1$—SH | $R^2$—$SO_2$—CH=$CH_2$ | $R^1$—S—$CH_2CH_2$—$SO_2$—$R^2$ |

In embodiments, the solvophobic portion of the compound is functionalized with a first click-reactive member and the compound to be attached thereto is functionalized with a second click-reactive member complementary to the first click-reactive member. The "click-reactive members" are meant to include those reactive members used in the processes known to those skilled in the art as Click chemistry.

Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitril oxides, azides, and diazoalkanes. Metal catalyzed click chemistry is an extremely efficient variant of the Huisgen 1,3-dipolar cycloaddition reaction between alkyl-aryly-sulfonyl azides, C—N triple bonds and C—C triple bonds which is well-suited herein. The results of these reactions are 1,2 oxazoles, 1,2,3 triazoles or tetrazoles. For example, 1,2,3 triazoles are formed by a copper catalyzed Huisgen reaction between alkynes and alkyl/aryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity as compared to the metal catalyzed reactions. Examples include DIFO and DIMAC. Reaction of the alkynes and azides is very specific and essentially inert against the chemical environment of biological tissues. One reaction scheme may be represented as:

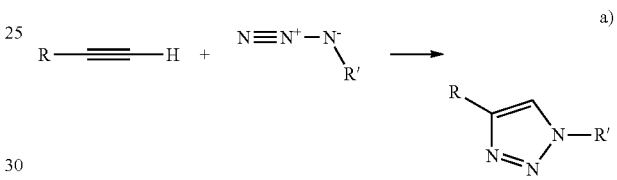

where R and R' are the activated compound and another compound (e.g., a bioactive agent).

The Diels-Alder reaction combines a diene (a molecule with two alternating double bonds) and a dienophile (an alkene) to make rings and bicyclic compounds. Examples include:

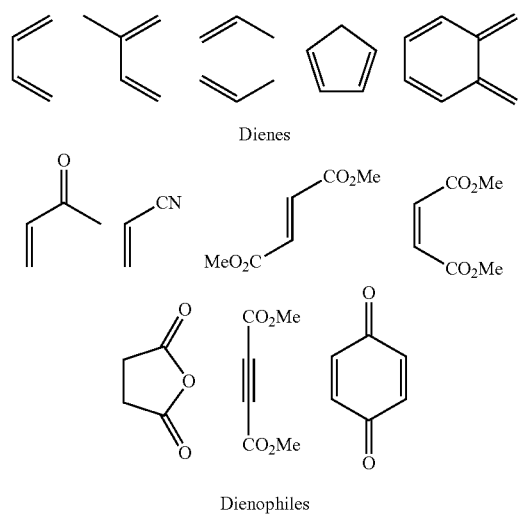

The thiol-alkene (thiol-ene) reaction is a hydrothiolation, i.e., addition of RS—H across a C=C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photo-polymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

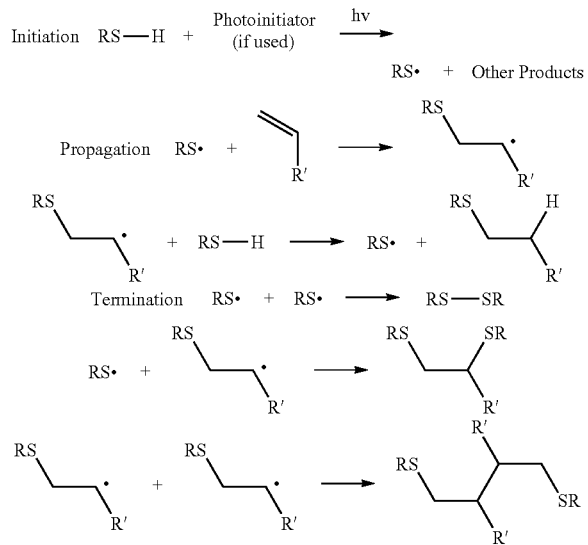

In embodiments, the solvophobic portion of the compound and a bioactive agent are functionalized to include a first click-reactive member which is an alkyne and a second click-reactive member which is an azide, respectively. In embodiments, the solvophobic portion of the compound or medical device and the bioactive agent are functionalized to include a first click-reactive member which is an azide and a second click-reactive member which is an alkyne, respectively. In yet other embodiments, the solvophobic portion of the compound or medical device and the bioactive agent are functionalized to include a first click-reactive member which is an azide and a second click-reactive member which is an alkene, respectively. See, van Berkel et al. *Cem Bio Chem,* 8, pages 1504-1508 (2007).

The first and second click-reactive members are intended to react and covalently bond the solvophobic portion of the activated compound to the functionalized bioactive agent at a physiologic pH. However, in some embodiments, the first and second click-reactive members may react quicker or more completely following the addition of a catalyst, such as a pH modifier, a metal ion catalyst or the introduction of heat or radiation. In embodiments, the addition of UV radiation may enhance the formation of a covalent bond between the first and second click-reactive members, especially where those groups are a thiol group and an alkene group. In embodiments, the addition of a metal catalyst, e.g., transition metal ions such as copper ions, may assist with the formation of a covalent bond between the first and second click-reactive members.

Bioactive Agents

The activated compounds may be covalently bonded to any of a variety of compounds functionalized with a second reactive member that is complementary to the first reactive member on the activated compound. In embodiments, the compound functionalized with a second reactive member is a bioactive agent functionalized with a second reactive member. Suitable bioactive agents include therapeutic, prophylactic or diagnostic agents. A wide variety of bioactive agents can be incorporated, either for delivery to a site, or to impart properties to the medical device, such as bioadhesion, cell attachment, enhancement of cell growth, inhibition of bacterial growth, anti-adhesion, and prevention of clot formation.

Examples of suitable therapeutic and prophylactic agents include synthetic inorganic and organic compounds, polymeric materials, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs such as antimicrobials, chemotherapeutics, anesthetics, and pain relievers. Other non-limiting examples include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes; cellular materials; and retroviral vectors for use in gene therapy. Representative diagnostic agents are agents detectable by x-ray, fluorescence, magnetic resonance imaging, radioactivity, ultrasound, computer tomography (CT) and positron emission tomography (PET).

Functionalizing the Compound and the Agent

The first and second reactive members may be positioned on the solvophobic portion of the compound and the compound to be attached thereto (e.g., a bioactive agent) using any variety of suitable chemical processes. With respect to the first and second reactive members on the solvophobic portion and bioactive agents respectively, it is contemplated that a plurality of first and second reactive members may be present and may be terminally located, or alternatively located along the length of the any portion thereof.

For example, monomers from which the solvophobic portion is made can be functionalized so that the reactive members appear along the length of the solvophobic portion. In such embodiments, the monomers can be initially functionalized with a member such as a halogen to provide a reactive site at which the desired first reactive member can be attached after polymerization. Thus, for example, a cyclic lactone (e.g., glycolide, lactide, caprolactone, etc.) can be halogenated and then polymerized using known techniques for ring opening polymerization. Once polymerized, the halogenated sites along the resulting polyester chain can be functionalized with the first reactive member. For example, the halogenated polyester can be reacted with sodium azide to provide azide groups along the polymer chain or with propagyl alcohol to provide alkyne groups along the polymer chain. See, R. Riva et al., *Polymer* 49, pages 2023-2028 (2008) for a description of such reaction schemes. In another example, a propargyl group may be introduce into a cyclic carbonate monomer to form 5-methyl-5-propargyloxycarbonyl-1,3-dioxan-2-one (MPC) which is polymerizable with lactide to form p(LA-co-MPC). See, Q. Shi et al., *Biomaterials,* 29, pages 1118-1126 (2008). Alternatively, a pre-formed biodegradable polyester can be halogenated by reaction with a non-nucleophilic strong base, such as lithium diisopropylamide, followed by electrophilic substitution with iodine chloride. The halogenated polyester is then reacted with sodium azide or propagyl alcohol to provide azide or alkyne groups, respectively. Other methods for functionalizing lactones are described in Jérôme et al., *Advanced Drug Delivery Reviews*, 60, pages 1056-1076 (2008). The entire disclosure of each of these articles is incorporated herein by this reference.

With respect to the solvophobic materials of the compound, it is contemplated that one or more than one first reactive members can be provided thereon. The process used to incorporate the first reactive members on the solvophobic material of the compound will be chosen based upon the nature of the solvophobic portion.

For example, where the solvophobic portion is based on a fatty acid, reactive members can be attached using the following synthetic route:

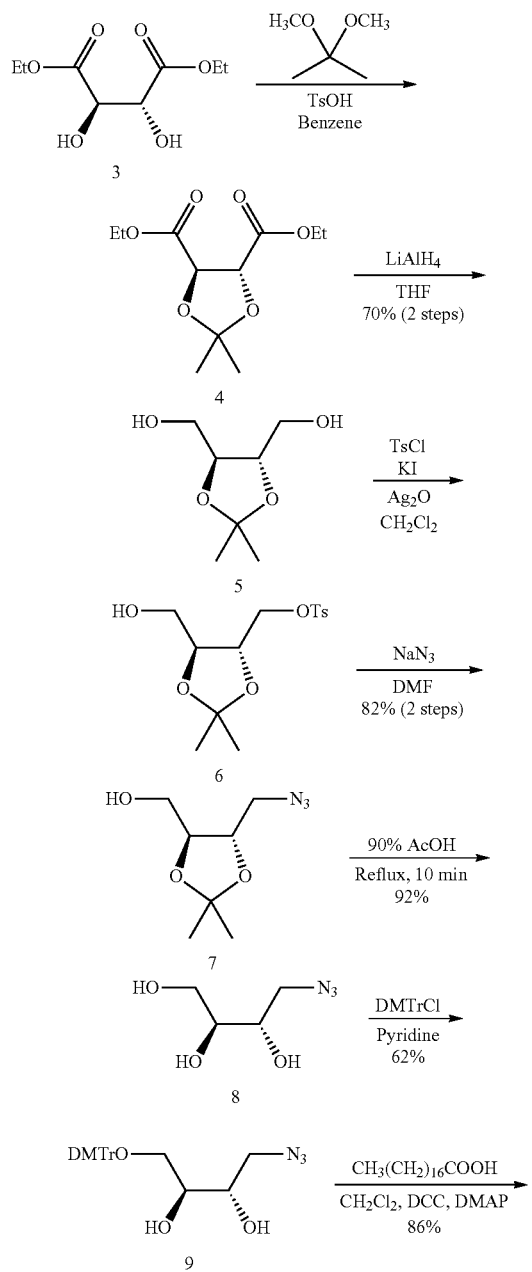

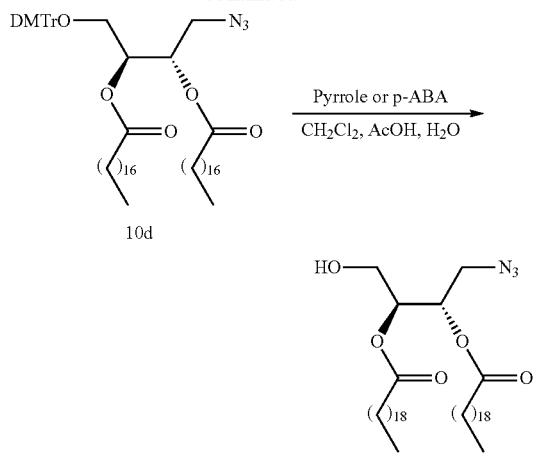

In embodiments, the diacids may be used to introduce the acyl chains (10d) which will provide for the synthesis of di-azide compounds.

In other embodiments where the solvophobic portion is based on a hydrophobic peptide, N-propargyl maleimide can be used to attach alkyne group (the second reactive members) on to the protein using to the thiol group as shown below:

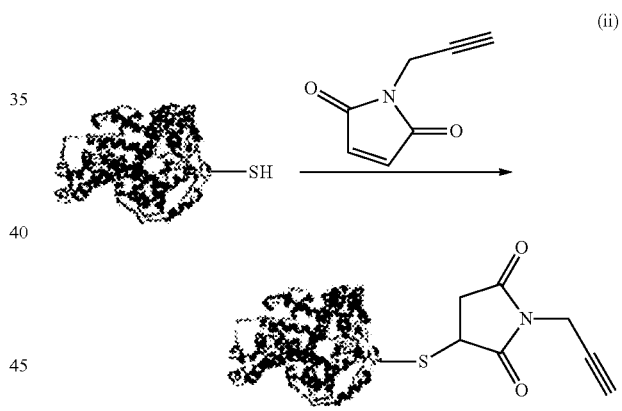

In other embodiments where the solvophobic portion is based on a hydrophobic peptide azide groups may be provided by conversion of the amino acid methyl ester to the corresponding azide via a Cu(II)-catalyzed diazotransfer reaction using triflic azide as shown in the following reaction scheme:

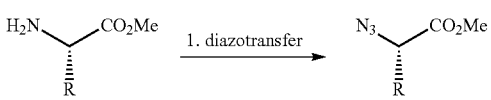

In yet other embodiments where the solvophobic portion is based on an oligosaccharide, reactive members can be attached using the following reaction scheme as described in detail in Zhang et al., Helvetica Chimica Acta—Vol. 91 pages 608-617(2008):

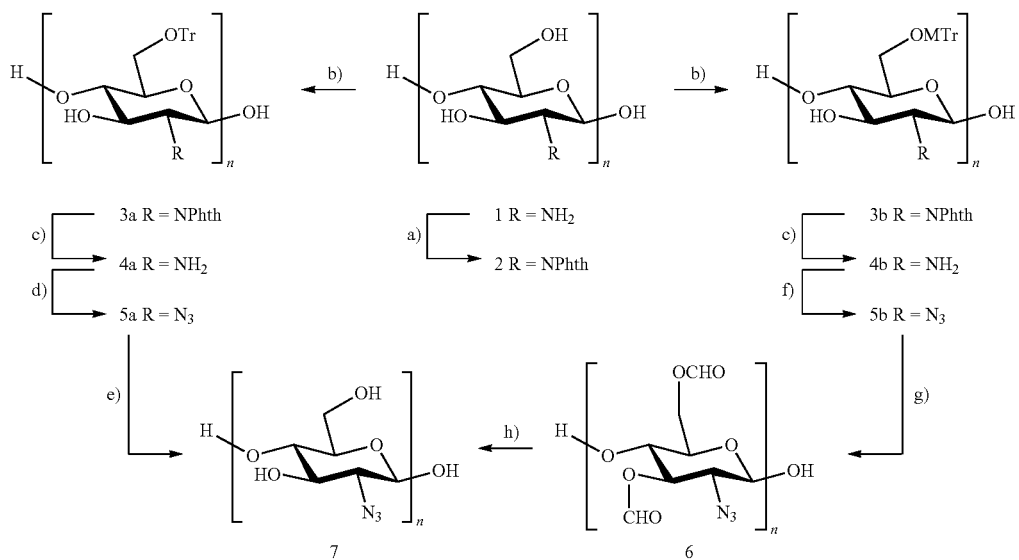

In embodiments, a plurality of different reactive members may be positioned on each of the solvophobic portion of the compound or medical device and the compound to be covalently bound thereto.

The Medical Device

The medical devices described herein include the combination of a solvent matrix and an activated compound including a solvophobic portion and a solvophilic portion, the solvophobic portion being functionalized with a first reactive member, wherein the solvophilic portion is positioned within the solvent matrix and the solvophobic portion including the reactive member is positioned outside, at or near the surface of the solvent matrix.

The solvent matrix and the compound may be combined, mixed or blended, to form the activated medical devices described herein. The solvophobic material of the compound will migrate to the outer portions of the solvent matrix while the solvophilic materials will attempt to migrate to the center of the solvent matrix. Because the solvophilic and solvophobic materials are covalently attached, varying degrees of migration are possible. In some embodiments, the solvophobic material will completely migrate outside the solvent matrix. In other embodiments, only a portion of the solvophobic material will be positioned outside the solvent matrix. The degree of migration will vary according to the materials chosen to form the compound and the solvent matrix.

The solvent matrix may represent from about 10% to about 99% of the medical device by weight. The solvent matrix may represent from about 25% to about 95% of the medical device by weight.

The activated compound may represent from about 5 to about 90% of the medical device by weight.

The medical device may be formed into any desired physical form. The medical device may include a solvent matrix which is polymeric and creates a polymeric substrate. The medical device may be fabricated for example, by extruding, melt processing, spinning, casting, molding, spray drying or any other fabrication technique known to those skilled in the art. The polymeric substrate may be made into any shape, such as, for example, a fiber, sheet, rod, staple, clip, needle, tube, foam, or any other configuration suitable for a medical device. Where the polymeric substrate is in the form of a fiber, the fiber may be formed into a textile using any known technique including, but not limited to, knitting, weaving, tatting and the like. It is further contemplated that the polymeric substrate may be a non-woven fibrous structure.

Any medical device suitable for implantation may be formed as described herein. Some non-limiting examples include monofilaments, multifilaments, surgical meshes, ligatures, sutures, staples, patches, slings, foams, pellicles, films, barriers, and the like.

In embodiments, the solvent matrix includes one or more polymers that can combined with the activated compound and melt extruded into fibers. In an illustrative process, one or more polymers making up the solvent matrix and the activated compound may be placed in a hopper and mixed thoroughly to provide substantially uniform distribution of the components. The components may be mixed using any conventional technique, with or without heating. For example, a mechanical mixer, a static mixer, or combinations thereof, may be employed to assist in providing a substantially uniform distribution of the components. After mixing, the mixture is extruded or spun to form one or more filaments.

Figure 5:
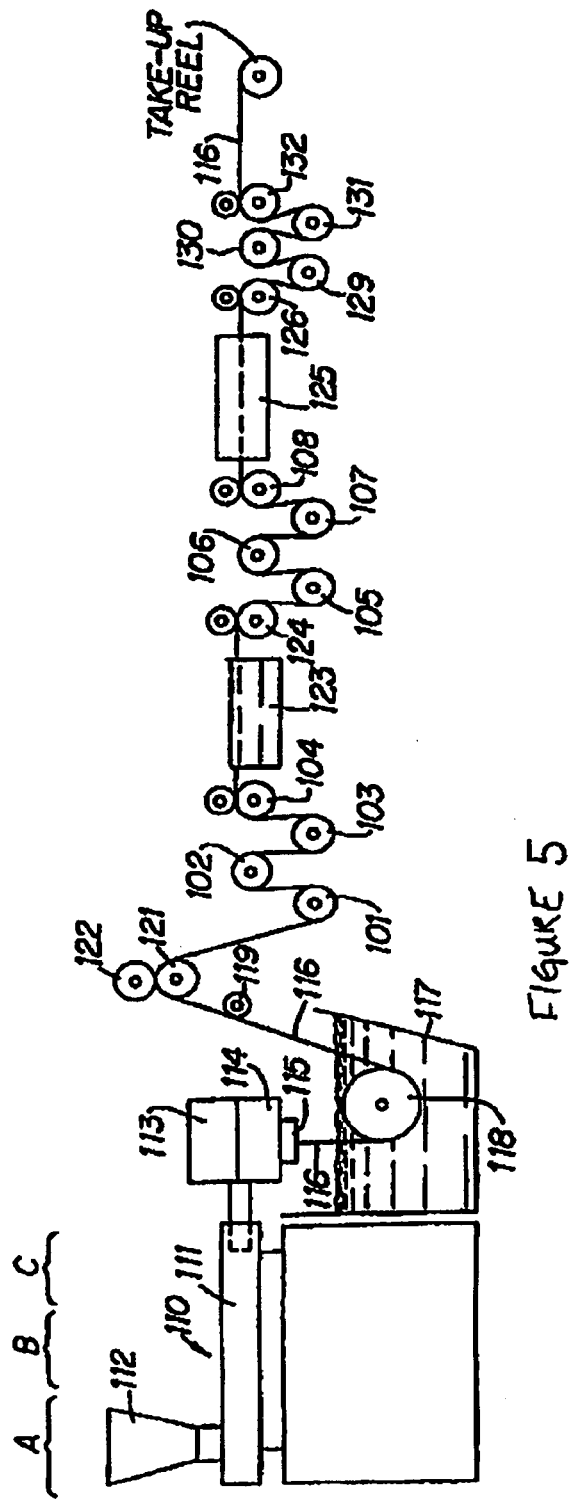
FIG. 5 is a schematic illustration of an apparatus which is suitable for carrying out a fiber manufacturing process in accordance with the present disclosure.

Known spinning apparatuses can be used for the production of filaments, in accordance with the present disclosure. FIG. 5 schematically illustrates a filament manufacturing operation in accordance with the disclosure. Extruder unit 110 is of a known or conventional types and is equipped with controls for regulating the temperature of barrel 111 in various zones thereof, e.g., progressively higher temperatures in three consecutive zones, A, B, and C along the length of the barrel. The first and second precursors to be spun into filaments are introduced to the extruder through hopper 112. Prior to or during placement in hopper 112, the first precursor is combined with the second precursor and mixed in a one-pot process. Adding heat during the mixing and/or extruding steps aids in the curing time of the first and second precursors, as faster curing rates are observed at higher temperatures.

Motor-driven metering pump 113 delivers the melt extruded first and second precursor mixture at a constant rate and with high pressure to spin pack 114 and thereafter through spinneret 115 possessing one or more orifices of desired diameter to provide a molten monofilament 116 which then enters quench bath 117, e.g., containing water, where the monofilament solidifies. The distance monofilament 116 travels after emerging from spinneret 115 to the point where it enters quench bath 117, i.e., the air gap, can vary. If desired, a chimney (not shown), or shield, can be provided to isolate monofilament 116 from contact with air currents which might otherwise affect the cooling of the monofilament in an unpredictable manner. In general, barrel zone A of the extruder can be maintained at a temperature of from about 100° C. to 220° C., zone B at from about 160° C. to 230° C. and zone C at from about 170° C. to about 240° C. Additional temperature parameters include: metering pump block 113 at from about 170° C. to about 230° C., spin pack 114 at from about 170° C. to about 230° C., spinneret 115 at from about 170° C. to about 230° C. and quench bath at from about 10° C. to about 80° C.

Monofilament 116 is passed through quench bath 117 around driven roller 118 and over idle roller 119. Optionally, a wiper (not shown) may remove excess water from the monofilament as it is removed from quench bath 117. On exiting the quench bath the monofilament is wrapped around a first godet 121 provided with nip roll 122 to prevent slippage which might otherwise result from the subsequent stretching operation; and subsequently wrapped around godets 101, 102, 103 and 104 or any other suitable godet arrangement. Monofilament 116 passing from godet 104 is stretched, e.g., with stretch ratios on the order of from about 3:1 to about 10:1 and preferably from about 4:1 to about 7:1, to effect its orientation and thereby increase its tensile strength.

In the stretching operation, monofilament 116 may be drawn through hot water (or other suitable liquid medium) draw bath 123 by means of godets 124, 105, 106, 107 and 108 or any other suitable arrangement of godets which rotate at a higher speed than godet 104 to provide the desired stretch ratio. The temperature of hot water draw bath 123 is advantageously from about 30° C. to about 90° C. and preferably is from about 30° C. to about 50° C. In an alternative stretching operation, generally preferred for smaller sutures sizes, e.g., sizes 3/0 to 8/0, monofilament 116 may be drawn by godets 124, 105, 106, 107, and 108 or any other suitable godet arrangement through hot air convection oven chamber 123 at a temperature of from about 30° C. to about 140° C., and preferably from about 50° C. to about 130° C. to provide the desired amount of stretch.

Following the stretching operation, monofilament 116 optionally may be subjected to an on-line annealing and/or additional stretching without shrinkage or relaxation with shrinkage operation as a result of which the monofilament shrinks. In the process of FIG. 1, on-line annealing with or without relaxation when desired is accomplished by driving monofilament 116 by godets 126, 129, 130, 131, and 132 or any other suitable godet arrangement through second hot air oven chamber 125 at a temperature of from about 40° C. to about 150° C., and preferably from about 60° C. to about 130° C. During the relaxation process, at these temperatures, monofilament 116 will generally recover to within about 80 to about 97 percent, and preferably to within about 95 percent, of its pre-annealed length to provide the finished suture. For relaxation, the third godet rotates at a slower speed than the second godet thus relieving tension on the filament.

Annealing of the suture also may be accomplished without shrinkage of the suture. In carrying out the annealing operation, the desired length of suture may be wound around a creel and the creel placed in a heating cabinet maintained at the desired temperature, e.g. about 60° C. to about 130° C. After a suitable period of residency in the heating cabinet, e.g., about 18 hours or so, the suture will have undergone essentially no shrinkage. Variables such as the annealing temperatures, time, and pressure may affect the curing time of the fibers as well. The creel may be rotated within the heating cabinet in order to insure uniform heating of the monofilament or the cabinet may be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures are then ready to be packaged and sterilized.

In embodiments, fibers from chitin or chitin derivative combined with an activated compound can be produced according to the present disclosure by spinning from anisotropic solution. Suitable methods for solution spinning chitin or chitin derivative fibers in general are disclosed in European Patent Nos. EP0328050A2 and EP0077098A2, the entire disclosures of which are incorporated herein by this reference. Such fibers can have tensile properties which typically fall between 4-8 g/d tenacity and 150-250 g/d initial modulus.

High strength chitosan fibers can be prepared by spinning an aniostropic solution containing chitosan or a derivative of chitin or chitosan and an activated compound through an inert gas and into a coagulating bath, removing the as-spun fiber and treating it with alkali to remove N-acetyl, O-acetyl or other pendant groups at the 2, 3 and 6 carbon positions of the glucosamine repeating unit. Treatment of fibers is by immersion of the fibers into a solution of NaOH. With fine denier fibers, e.g., 4-5 dpf., a 5 minute immersion at 70° C. in a 50% wt. solution of NaOH is satisfactory. A 2-3 hr. exposure at 80° C. in a 30% wt. solution is useful with chitosan acetate formate fiber. With chitosan acetate, temperatures in the range of 80° to 116° C. at NaOH concentration of 30% have been found useful with the higher temperatures requiring less time for completion of the reaction. Severe treatments are generally to be avoided since they may cause excessive interfilament fusion and a product of inferior quality. Conversion of the starting fiber to a chitosan fiber is confirmed if the chitosan fiber is readily soluble in dilute (3-20% wt.) acetic acid.

Figure 6:
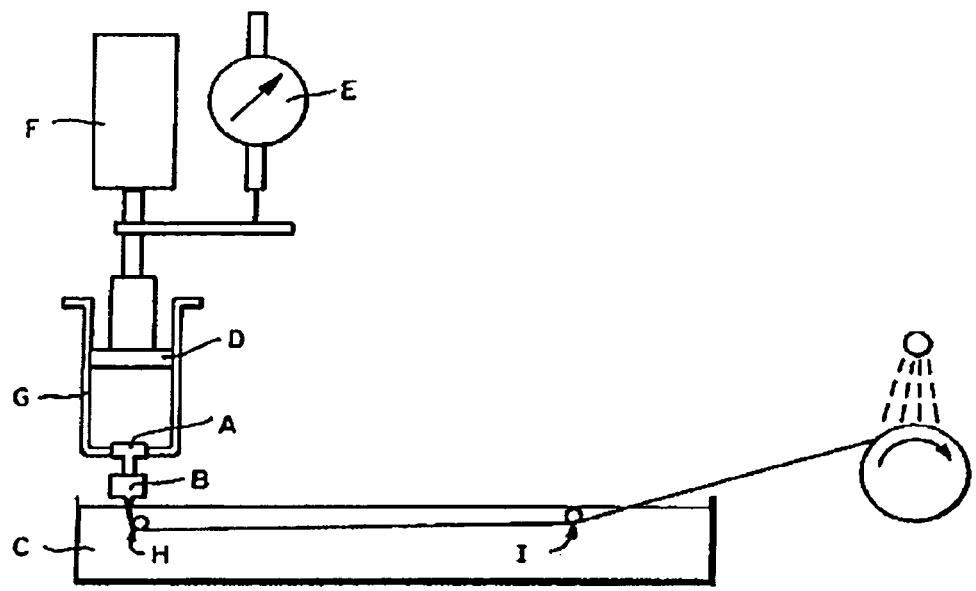
FIGS. 6 and 7 schematically illustrate apparatus suitable for carrying out an alternate fiber manufacturing process in accordance with the present disclosure.

In using the apparatus of FIG. 6 an anisotropic solution of chitin or a chitin derivative is placed in spin cell (G). A piston (D) activated by hydraulic press (F) and associated with piston travel indicator (E) is positioned over the surface of the solution, excess air is expelled from the top of the cell and the cell is sealed. The spin cell is fitted at the bottom with the following screens (A) for solution filtration: four to six 325-mesh screens. The filtered solution is then passed into a spinneret pack (B) containing two or three 325-mesh screens. Solutions are extruded through an air gap at a controlled rate into a static bath (C) using a metering pump to supply pressure at piston (D). The fiber is passed around a pin (H), pulled through the bath, passed under a second pin (I) and wound onto a bobbin. The air gap between the spinneret face and the coagulation bath is typically 0.6 to 2.0 cm. The coagulation bath temperature is generally held below 100° C.

Figure 7:
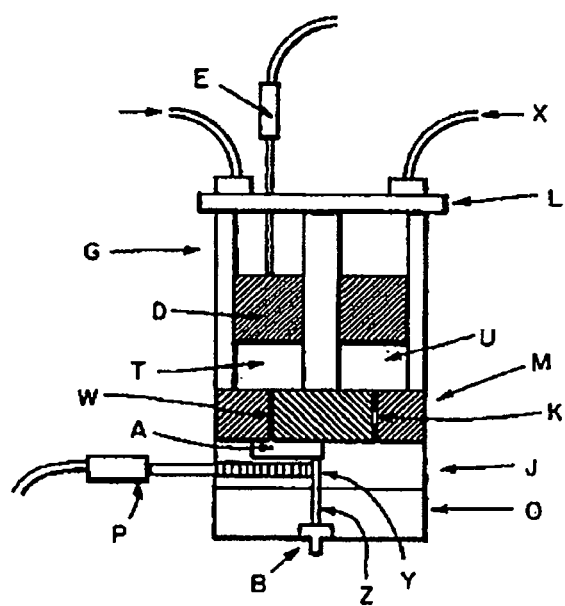

In using the apparatus of FIG. 7, filter plate (J) is replaced by mixing plate (R). Polymer dope is placed in cylinder bore (T) and then piston (D) and cap plate (L) is fitted to the spin cell (G). A driver fluid (e.g. water) is pumped into the upper part of bore (T) through feed line (F). The piston (D) is displaced by the driver fluid, thereby pushing the polymer dope through passages (W), (S) in mixing plate (R) and then through passage (K) in distribution plate (M) into second cylinder bore (U). This process is then reversed by pumping fluid through feed line (X). The aforementioned forward and reverse process is repeated several times to effect a mixing of the polymer dope. Component (E) acts to sense the position of cylinder (D).

After mixing is complete (about 30 cycles), mixing plate (R) is replaced by filter plate (J) and polymer dope is extruded from bore (T) through passage (W), through filter pack (A) containing 2 Dutch Twill Weave 165×800 mesh screens, through passage (Y) in filter plate (J) and passage (Z) in spinneret mounting plate (O) and out of spin cell (G) through spinneret (B). The extruded dope is spun into a bath and taken up as described for FIG. 2. Pressure of the polymer dope during spinning is measured by pressure transducer (P).

In other embodiments, fibers from collagen or collagen derivatives mixed with an activated compound can be produced according to the present disclosure by gel spinning. Suitable methods for gel spinning collagen fibers in general are disclosed in U.S. Pat. Nos. 5,562,946 and 5,911,942, the entire disclosures of which are incorporated herein by this reference.

Figure 8:
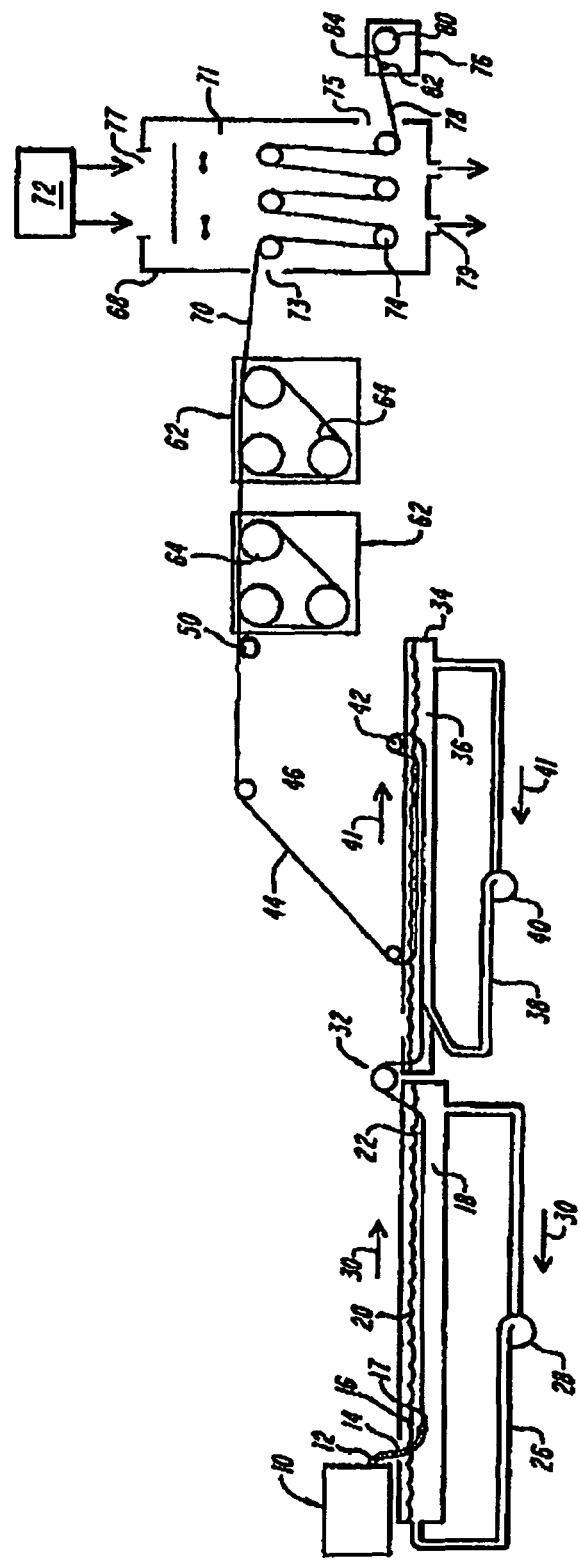
FIG. 8 schematically illustrate another apparatus suitable for carrying out a fiber manufacturing process in accordance with the present disclosure.

In an illustrative apparatus for gel spinning such fibers shown in FIG. 8, collagen reservoir chamber 10 holds a liquid solution containing collagen and the activated compound. In one embodiment, a suitable chamber is a stainless steel syringe. Reservoir tube 12 is attached to collagen reservoir chamber 10 for directing collagen solution from collagen reservoir chamber 10 through infusion pump 14 to spinneret 16. Infusion pump 14 is capable of raising the pressure of the collagen material such that it can be extruded through spinneret nozzle 17 of spinneret 16. In embodiments, a positive displacement metering pump is used. Spinneret 16 can be single bore or multiple bore to produce monofilament or multifilament fibers respectively. The spinneret bores can be of various diameters or have tapered profiles to form fibers of different sizes and tensile strengths. Co-component fibers can be produced with other specialized spinnerets as are known in the art. In one embodiment, spinneret nozzle 17 has diameters in the range of between about 100 and 1,000 microns.

Coagulation bath 18 has a coagulation solution 20 that can cause the liquid collagen to form a collagen gel, such as a 0.75% alkaline alginic acid in a boric acid buffer or sugar solutions or polyethylene glycol solution which also has hydrophilic properties. The opening of spinneret is immersed in a flowing coagulation solution 20. Coagulation bath 18 is suitably sized for allowing extrusion of fiber from spinneret 16 through coagulation solution 20 while having a sufficient residency time for collagen gel fiber 22 to form. Coagulation bath 18 can be heated and instrumented for monitoring the relevant process variables, such as temperature, pH and velocity. Coagulation bath 18 allows collagen gel fiber 22 to be formed in a horizontal trough or in a tube or vertically in a tube. Coagulation bath 18 is configured to allow circulation of coagulation solution 20 through recirculating loop 26 by circulating pump 28. Coagulation bath flow can be in the same direction 30 of fiber travel. At the end of the coagulation bath 18, roller 32 is for directing fiber out of the coagulation bath. Roller 32 is motorized and can be activated to wind collagen gel fiber 22 and subsequently tow collagen gel fiber 22 at desired speeds.

Dehydrating bath 34 is adjacent to roller 32 and coagulation bath 18 and is configured to allow fiber 22 to be drawn into dehydrating bath 34 from roller 32. Dehydrating bath 34 holds dehydrating solution 36, such as 90% ethanol, which allows further dehydration and annealing of the fiber and promotes polymerization of the collagen to improve fiber strength. An example of another suitable dehydration solution composition is acetone. Dehydrating bath 34 is configured to allow variable circulation of dehydrating solution 36 through recirculating loop 38 by circulating pump 40 which can be adjusted directionally, such as direction 41 or in the opposite direction. Return rollers 42, which can be near each end of dehydrating bath 34, allow the fiber path to be lengthened by doubling back to make any number of multiple passes through dehydrating bath 34 to allow further dehydration and promote polymerization of the collagen.

Partially dehydrated fiber 44 is wound around roller 46 to second roller 50 and then to stretching roller means 62, wherein the fiber can undergo a controlled deformation by being stretched between two groups of rollers 64 rotating at slightly different rates of speed. The speed of rotation of rollers 64 can be precisely controlled with digital microprocessors arranged in a closed feedback loop. The fibers are wrapped around each roller 64 several times to prevent fiber slippage relative to the roller surfaces. Roller 64 surfaces can made of a polymer or a hardened metal resistant to corrosion. Roller 64 rotations can be adjusted individually to allow the fiber to be stretched beyond the elastic yield point to produce a longer fiber of reduced diameter. Stretching roller means 62 can operate under semi-dry or dry conditions and also under high moisture content atmosphere.

Drying cabinet 68 has opening 73 for receiving stretched fiber 70 from stretching rollers 62. Drying cabinet 68 has passage 71 through drying cabinet 68 for receiving warm, dry filtered air or a dry inert gas, such as dry nitrogen gas, from gas source 72 at a suitable temperature and humidity for drying stretched fiber 70. The air can be passed through air passage opening 77 into passage 71 and exiting from air passage opening 79. In embodiments, the temperature of the air is between about 35° C. and 39° C. The humidity is in the range of between 10 and 20 percent relative humidity. Drying cabinet 68 has a series of rollers 74 which allows stretched fiber 70 to remain in drying cabinet 68 while being rolled, thereby increasing the residence time of fiber 70 in drying cabinet 68. Drying cabinet rollers 74 are adjustable in distance between each other and to compensate for the fiber line speed. Drying cabinet rollers 74 can be driven at a surface roller speed that can be synchronized with that of stretching roller means 62. Drying cabinet 68 has a door to provide access to the rollers for threading the leader thread.

Take-up winder 76 is for receiving dried fiber 78 from exit 75 of drying cabinet 68. Take-up winder 76 has spool 80 for receiving dried fiber on a removable spindle bobbin. Take-up winder 76 has a slip clutch 82 to provide a constant fiber line tension and fiber line speed as the spooled fiber rotates radially around spool 80. Fiber spool 80 can wind the fiber level or by randomly winding with the take-up winder 76.

Fibers formed in accordance with the present invention may be used for a variety of surgical and wound applications. The fibers, for example, may be used alone, such as for example, for closing wounds and incisions in the form of monofilament or multifilament sutures. Multifilament sutures may be constructed using any technique within the purview of those skilled in the art, such as spinning and braiding the fibers together. The fibers may also be used in combination with the other absorbable or non-absorbable fibers to form multifilament sutures or to form knitted, woven, or non-woven meshes or fabrics. A wide variety of surgical articles can be manufactured from the fibers of the present disclosure. These include but are not limited to sutures as discussed above, threads, rods, filaments, yarns, meshes, slings, patches, wound dressings, drug delivery devices, fasteners, and other implants and composite materials, such as pledgets, buttresses, adhesion barriers, and the like.

Various modifications and variations of the polymers, amphiphilic compounds, medical devices, click-reactive members and processes described herein will be apparent to those skilled in the art from the foregoing detailed description. Such modifications and variations are intended to come within the scope of the following claims.

What is claimed is:

1. A medical device comprising a hydrophilic solvent matrix and a compound including a solvophobic material and a solvophilic material, the solvophobic material is functionalized with a first reactive member, wherein the solvophilic material is positioned within the solvent matrix and the solvophobic material including the first reactive member is positioned outside the solvent matrix.

2. The medical device of claim 1, wherein the first reactive member is an electrophilic group.

3. The medical device of claim 1, wherein the first reactive member is a nucleophilic group.

4. The medical device of claim 1, wherein the first reactive member is an alkyne group.

5. The medical device of claim 1, wherein the first reactive member is an azide group.

6. The medical device of claim 1, wherein the solvent matrix is selected from the group consisting of a solid, a gel and a liquid.

7. The medical device of claim 1, wherein the solvophilic material includes polyamides, hydrophilic polyurethanes, polylactones, polyimides, polylactams, poly-vinyl-pyrrolidone, polyvinyl alcohols, polyacrylic acid, polymethacrylic acid, poly(hydroxyethyl methacrylate), gelatin, dextran, oligosaccharides, chitosan, hyaluronic acid, alginate, chondroitin, mixtures and combinations thereof.

8. The medical device of claim 1, wherein the solvophobic material includes polyethylene, polypropylene, hydrophobic polyurethanes, polyacrylates, polymethacrylates, fluoropolymers, polycaprolactone, polylactide, polyglycolide, phospholipids, and polyureas, poly(ethylene-vinyl acetate), polyvinylchloride, polyesters, polyamides, polycarbonate, polystyrenes, polytetrafluoroethylene, silicones, siloxanes, fatty acids, and chitosan having high degrees of acetylation and mixtures and combinations thereof.

9. The medical device of claim 1, further comprising a bioactive agent functionalized with a second reactive member, said bioactive agent being covalently bound to said solvophobic material by means of said first reactive member covalently bonding with said second reactive member.

10. The medical device of claim 9, wherein the second reactive member is an azide group.

11. The medical device of claim 9, wherein the second reactive member is an alkyne group.

12. The medical device of claim 9, wherein the second reactive member is an alkene group.

13. The medical device of claim 9, wherein the second reactive member is a nucleophilic group.

14. The medical device of claim 9, wherein the second reactive member is an electrophilic group.

15. The medical device of claim 1, wherein the solvophilic material is chitosan.

16. The medical device of claim 15, wherein the solvophilic material is chitosan having a degree of acetylation from 0 to about 30% and the solovophobic material is chitosan having a degree of acetylation greater than about 50%.

17. The medical device of claim 1, wherein the solvophilic material is covalently bonded to the solvophobic material.

18. The medical device of claim 1, wherein the medical device is a fiber.

19. The medical device of claim 18, wherein the fiber is used to form a textile.

* * * * *